(12) United States Patent
Lewis et al.

(10) Patent No.: US 12,064,664 B2
(45) Date of Patent: Aug. 20, 2024

(54) METHOD AND SYSTEM FOR DYNAMICALLY TRANSFORMING USER HEALTH AND EXERCISE-RELATED DATA INTO VISUAL, AUDIO, TEXTUAL, AND PHYSICAL DATA REPRESENTATIONS

(71) Applicant: Willowview Consulting, LLC, Eagle, ID (US)

(72) Inventors: Layne Ellen Lewis, Eagle, ID (US); Nick Morris, Redondo Beach, CA (US); James Shaver, Boise, ID (US); Robert Holloman Walker, Deltaville, VA (US)

(73) Assignee: Willowview Consulting, LLC, Eagle, ID (US)

( * ) Notice: Subject to any disclaimer, the term of this patent is extended or adjusted under 35 U.S.C. 154(b) by 384 days.

(21) Appl. No.: 17/354,415

(22) Filed: Jun. 22, 2021

(65) Prior Publication Data
US 2022/0143460 A1 May 12, 2022

Related U.S. Application Data

(60) Provisional application No. 63/111,886, filed on Nov. 10, 2020.

(51) Int. Cl.
*A63B 24/00* (2006.01)
*A63B 71/06* (2006.01)
(Continued)

(52) U.S. Cl.
CPC ...... *A63B 24/0006* (2013.01); *A63B 24/0062* (2013.01); *A63B 24/0075* (2013.01);
(Continued)

(58) Field of Classification Search
CPC ............ A63B 24/0006; A63B 24/0062; A63B 24/0075; A63B 71/0622;
(Continued)

(56) References Cited

U.S. PATENT DOCUMENTS 10,798,547 B2 * 10/2020 Gold .................. G06Q 30/0207
2011/0201943 A1    8/2011 Beck et al.
(Continued)

FOREIGN PATENT DOCUMENTS

CN          201208257 Y  *  3/2009
WO    WO 2020/185699        9/2020

OTHER PUBLICATIONS

Crevier, Lynn M. "Wearable technology provides readymade monitoring for musculoskeletal rehabilitation." The Journal of Musculoskeletal Medicine 26.5: 178. CMP Medica, LLC. (May 2009) (Year: 2009).*

*Primary Examiner* — Linh Giang Le
(74) *Attorney, Agent, or Firm* — Hawley Troxell Ennis & Hawley LLP; Rivkah Young

(57) ABSTRACT

Various technological methods are utilized to collect user health and exercise-related data from one or more users of an application and the collected user data and user activity data is utilized to generate visual, audio, textual, and/or physical data representations, which may be provided to the one or more users either dynamically in real-time during an activity, such as a physical exercise activity, or may be provided to the one or more users after the completion of one or more activities.

23 Claims, 15 Drawing Sheets
(8 of 15 Drawing Sheet(s) Filed in Color)

(51) Int. Cl.
*G06N 7/00* (2023.01)
*G16H 20/30* (2018.01)
*G16H 10/60* (2018.01)

(52) U.S. Cl.
CPC ........... *A63B 71/0622* (2013.01); *G06N 7/00* (2013.01); *G16H 20/30* (2018.01); *A63B 2024/0009* (2013.01); *A63B 2024/0065* (2013.01); *A63B 2024/0068* (2013.01); *A63B 2024/0081* (2013.01); *G16H 10/60* (2018.01)

(58) Field of Classification Search
CPC .... A63B 2024/0009; A63B 2024/0065; A63B 2024/0068; A63B 2024/0081; G06N 7/00; G16H 20/30; G16H 10/60; G16H 50/20
See application file for complete search history.

(56) References Cited

U.S. PATENT DOCUMENTS

| 2014/0200874 A1 | 7/2014 | Zeng et al. | |
| 2015/0073720 A1* | 3/2015 | Altini | A61B 5/6802 702/19 |
| 2015/0157256 A1 | 6/2015 | Galeev | |

* cited by examiner

| Raw User Data | Available Values | Color | Defined By |
|---|---|---|---|
| Exercise Intensity | 0–10 | Red | Entered Data and/or Measured Data |
| Mood | 0–10 | White to Black | Entered Data |
| Nutrition | 0–10 | Green | Entered Data and/or Measured Data |
| Sleep Quality | 0–10 | Yellow | Entered Data and/or Measured Data |
| Motivation | 0–10 | Blue | Entered Data |

METHOD AND SYSTEM FOR DYNAMICALLY TRANSFORMING USER HEALTH AND EXERCISE-RELATED DATA INTO VISUAL, AUDIO, TEXTUAL, AND PHYSICAL DATA REPRESENTATIONS

RELATED APPLICATIONS

This application claims the benefit of Lewis et al, U.S. Provisional Patent Application No. 63/111,886, filed on Nov. 10, 2020, entitled "METHOD FOR INTERPRETING HEALTH AND EXERCISE-RELATED DATA FROM VARIOUS SOURCES ENABLE EXERCISE TO BE A SOURCE OF ENERGY TRANSFER/RECYCLE/RE-IMAGINATION AND PRODUCING A REAL-TIME ARTISTIC REPRESENTATION OF DATA USING VISUAL, AUDIO OR WRITTEN OUTPUT," which is hereby incorporated by reference in its entirety as if it were fully set forth herein.

BACKGROUND

Technology continues to advance at a rapid rate, and as a result, more and more people are making fundamental changes to the way that they work, live, and play. Engaging in remote activities is becoming increasingly common, however, a lack of in-person connection with co-workers, friends, and family, often leads to feelings of isolation, loneliness, and depression in many individuals. As a result, the increasing shift to remote activities is having a major impact on the health, well-being and quality of life for millions of people. Global health concerns, such as the COVID-19 pandemic have further expedited the shift to a world in which many daily life activities will be performed in relative isolation. According to some studies, the increasing shift to activities performed in isolation has tripled the rate of depression in US adults in all demographic groups, especially in those with financial worries and/or physical disabilities.

With all of the changes that people have been required to make to adjust to the new socially distanced, remote life reality, it has become increasingly important for individuals and groups to stay socially connected and to maintain their physical and mental health. Studies have shown that feelings of extreme loneliness are associated with increased risk of physical and mental health problems. Examples of such physical and/or mental health problems may include, but are not limited to high blood pressure, diabetes, arthritis, depression, stress, and anxiety. As more and more people increase their risk of feeling extreme loneliness, it is critical to look for ways to avoid, prevent, and improve problems associated with people's mental and physical health. One of the methods that has been proven over time to prevent and/or improve these physical and/or mental health problems involves exercising regularly. As one example, research on depression, anxiety and exercise has shown that the psychological and physical benefits of exercise can help improve mood and reduce anxiety. Working out and other forms of physical activity can ease symptoms of depression or anxiety and increase feelings of overall well-being. Some studies show that, once an individual's symptoms of depression and anxiety have abated, exercise may also prevent the symptoms of depression and anxiety from returning.

Exercising has been shown to start a biological cascade of internal events that often result in many health benefits, such as, but not limited to, protecting against heart disease and diabetes, improving sleep, and lowering blood pressure. High-intensity exercise releases the body's "feel-good" chemicals, endorphins, which often results in the "runner's high" that many people who jog and/or run regularly report. For those who do not participate in high-intensity exercise, value is typically found in low-intensity exercise sustained over time. This kind of activity has been shown to spur the release of proteins called neurotrophic or growth factors, which cause nerve cells to grow and make new connections. This results in an improvement in brain function, which helps to regulate mood and relieve psychological issues such as, but not limited to depression, stress, and anxiety.

Psychological issues, such as depression, stress, and anxiety often manifest physically by causing disturbed sleep, reduced energy, appetite changes, body aches, and increased pain perception, all of which can result in less motivation to exercise, and less exercise can in turn exacerbate the psychological issues. This cycle can be very hard to break, however research has shown that getting up and moving, even in small amounts, can often go a long way to helping break the cycle.

One group of people particularly affected by this cycle are those with a physical and/or mental disability. The National Institute on Disability, Independent Living and Rehabilitation Research (NIDILRR), as the primary funder of disability, independent living, and rehabilitation research, recognizes the need for people with disabilities to have access to consistent, high-quality services to accomplish their personal goals, and to lead active lives. Most people with disabilities want access to the same things as their able-bodied peers, however many of the currently available exercise solutions are not easily adaptable for persons with disabilities or physical limitations. It is clear from research that people with limited mobility see great benefits when participating in various exercise programs. Some of these benefits may include, but are not limited to, an increase in aerobic capacity, an increase in lower extremity bone mass, an improvement in blood lipid profile, an improvement in sleep quality, an improvement in mobility and independence, as well as a decline in depression, anxiety, fatigue and pain.

While it has been shown that exercise may be as effective as medications to fight depression, many traditional exercise activities, programs, and/or routines often focus on measuring effort and immersion, and typically utilize competition-based methodologies, such as, but not limited to step counting, which may actually add to symptoms of depression, stress, frustration, and lowered feelings of self-worth, for example, if an individual sets a goal for a particular day but is not able to achieve the goal. This, in turn, can lead to a loss of commitment and motivation to sustain physical activity. While this is true of most people in general, it is especially true of those with physical injuries or disabilities, in part because many individuals associate physical pain and/or discomfort with certain physical activities, and thus, staying motivated and committed to an exercise or physical rehabilitation routine may prove especially painful and/or difficult.

Further, and especially noticeable in the sports world, the activity of individuals and teams of individuals is typically measured by vast quantities of numbers and statistics, which can lead individuals to feel depressed and/or discouraged due to the fact that their self-worth is being determined by a set of numerical values. This type of competitive and numerical based evaluation of physical activity often leaves many individuals feeling that their contributions are not valuable, which can lead to greater feelings of emotional and physical distress.

Additionally, doctors and mental health researchers continue to find evidence that our ability to foster healthy and meaningful relationships, as well as our ability to feel that we are occupying a valuable place in society, plays a huge role in determining our vulnerability to anxiety, stress, depression, mental illness, and/or addiction. Having healthy relationships and fulfilling our needs for positive social interaction does not often come easily, and in many cases requires active introspection and a therapeutic approach, specifically for individuals struggling to heal from past physical and/or psychological pain. For those that suffer from physical disabilities, and/or mental disabilities such as anxiety, stress, depression, mental illness, and addiction, this internal work is often entirely necessary and worthwhile in order to create opportunities for personal joy and meaningful social connections.

Psychological research has found that most people need to experience two types of connection in their lives to heighten their overall sense of well-being and satisfaction. The first is a deep connection between two people. This may occur between two friends, romantic partners, or family members. The second type of connection is a feeling of belonging to a social group. This may be a group of close friends, a tight-knit group of colleagues, or a religious circle. These groups tend to share common goals, and provide a kind of connection that greatly improves a person's capacity for satisfaction and fulfillment in their life.

Thus, for all individuals, whether they are in good health or whether they have physical and/or mental conditions or disabilities, maintaining healthy activity routines and healthy social connections are key components to ensuring that these individuals are able to achieve overall well-being and a high quality of life. As noted above, the trend of socially distancing, and the increase in remote activity participation, exacerbates a variety of physical and/or psychological conditions, which has hindered the ability for large numbers of people to maintain healthy activity routines and/or healthy social connections.

Exercise can in many ways help people to cope with feelings of depression, loneliness and isolation, however, currently utilized motivational models based on performance and improvement metrics often fail to motivate individuals over time. As noted above, health data, physical activity data, and exercise/performance related data is typically measured in numerical values and statistics, and when this data is presented to individuals, it often takes the form of numbers, charts, and graphs, which do little to motivate and inspire, and can readily lead to frustration, discouragement, and loss of motivation for many individuals. Engaging in group exercises, feeling a sense of community, and working with others towards a common goal, not only helps to motivate people, but also addresses a wide variety of social, psychological, and physical issues.

What is needed, therefore, is a solution that utilizes technological innovations to address the technical issues inherent in the problem of inspiring and motivating individuals to maintain healthy lifestyles while engaging in activities that foster the growth and development of social connections, especially for individuals in relatively isolated environments.

SUMMARY

Embodiments of the present disclosure provide a technical solution to the issues discussed above by utilizing technological innovations to transform health and exercise-related data received and/or collected from individuals into one or more individualized, unique and/or artistic data representations in order to inspire and motivate individuals to maintain healthy lifestyles while engaging in activities that foster the growth and development of social connections through participation in a shared artistic goal.

In one embodiment, the system and method disclosed herein uses various technological methods to collect user data and user activity data, such as health and exercise-related data, from one or more users of an application and the user data and user activity data is utilized to generate a variety of visual, audio, textual, and/or physical data representations, which may be provided to the one or more users either dynamically in real-time during an activity, such as a physical exercise activity, or may be provided to the one or more users after the completion of one or more activities. The goal is to help inspire and motivate individuals to maintain healthy exercise, nutritional, and social routines by providing the users with dynamically generated individualized and/or artistic data representations that are unique to one or more activity sessions of a particular user and/or particular group of users. In one embodiment, a group of users may generate artistic data representations collaboratively, for example, with each individual in the group contributing to a portion of the data representation.

As noted above, many traditional exercise and health-related applications utilize a numerical and/or competition-based methodology to motivate individuals, which often subtracts from an individual's state of mind, for example, when the individual is not able to meet predefined goals. This type of methodology often creates feelings of discouragement instead of motivation, especially among individuals with physical and/or psychological disabilities. In contrast, the data representations generated by the method and system disclosed herein present positive affirmation and progress to application users, which shows appreciation and awareness of what users' bodies are accomplishing, regardless of the size of the accomplishment. In various embodiments, presenting a user, especially a user with a disability, with positive and diverse affirmations can help to slow the decline of an individual's sensory, communicative, and/or mental functions, which can help to maximize an individual's performance in community living situations. In various embodiments, the data representations generated by the method and system disclosed herein may dynamically change during the course of an exercise session, and a user may also be able to view the data representations as they change and/or grow over time, for example, over the course of a single activity session, or over the course of a year.

As noted above, in one embodiment, the data representations generated by the method and system disclosed herein are created collaboratively with other application users, such that multiple users can contribute multiple data inputs to the data representations, which helps to foster the growth and development of social connections through participation in a shared artistic goal.

In some embodiments, the technology utilized by the method and system disclosed herein can be provided to an application user on a special-purpose device, however, in other embodiments, the technology utilized herein pairs with devices that most people already use daily, such as, but not limited to, cell phones or smart watches. In one embodiment, the user data and user activity data may be collected from user data entry, in other embodiments, the user data and user activity data may be collected using a variety of biomedical sensors affixed to the user's body and/or sensors in close proximity to the user's body, sensors on a device associated with the user, such as a mobile phone, and/or sensors on a machine associated with the activity being performed, such as an exercise bike. In various embodiments, user data and user activity data may be collected using a variety of human machine interface (HMI) mechanisms.

As a result of these and other disclosed features, which are discussed in more detail below, the disclosed embodiments provide an effective and efficient technical solution to the technical problem of transforming health and exercise-related data received and/or collected from individuals into one or more individualized, unique and/or artistic data representations in order to inspire and motivate individuals to maintain healthy lifestyles while engaging in activities that foster the growth and development of social connections through participation in a shared artistic goal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 11 is a table showing a simplified example of one way that raw user data can be mapped to colors of a visual and/or physical data representation, in accordance with one embodiment.

Figure 1:
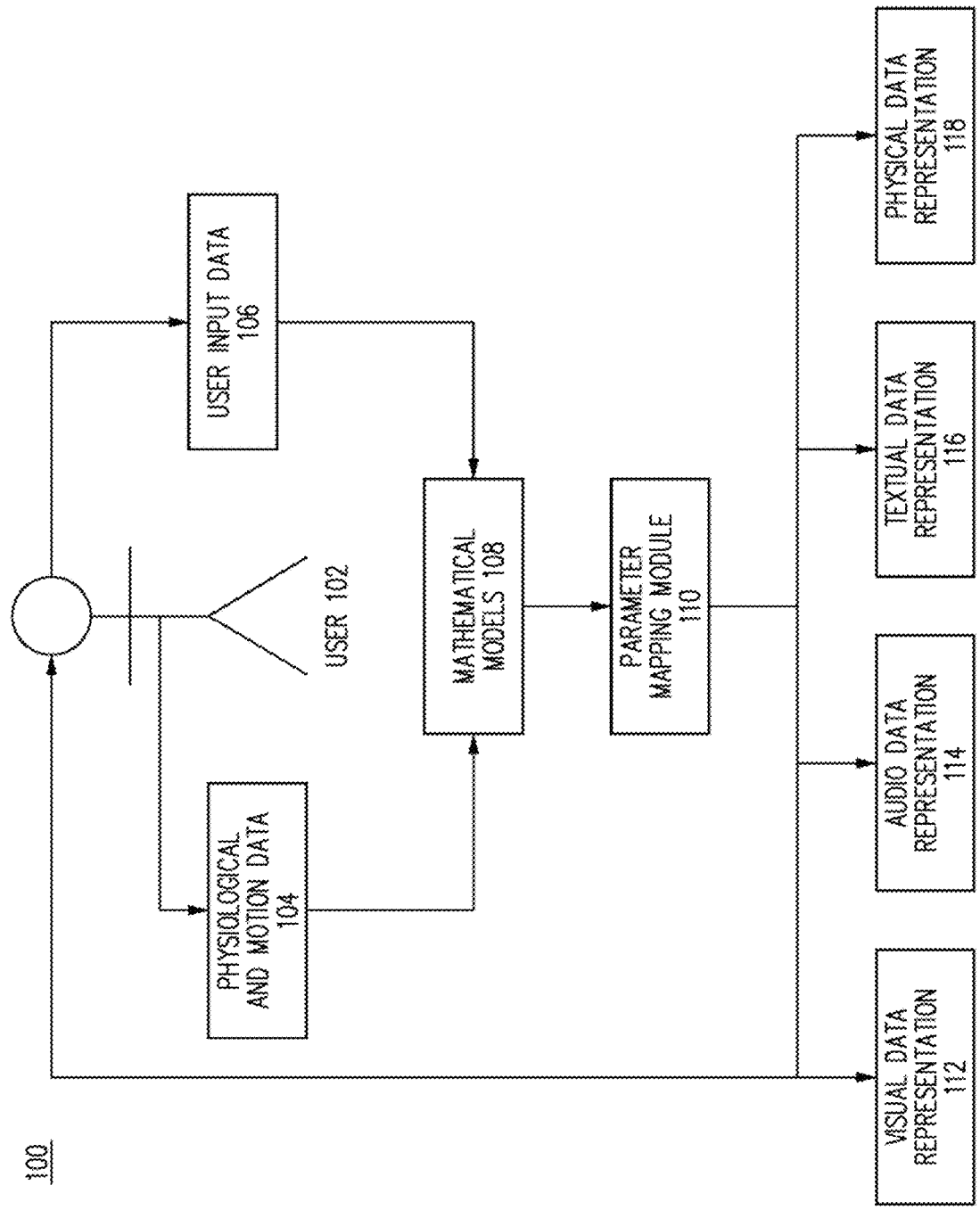
FIG. 1 is an overview of a method and system for transforming user data and user activity data into various data representations, in accordance with one embodiment.

Common reference numerals are used throughout the figures and the detailed description to indicate like elements. One skilled in the art will readily recognize that the above figures are merely illustrative examples and that other architectures, modes of operation, orders of operation, and elements/functions can be provided and implemented without departing from the characteristics and features of the invention, as set forth in the claims.

DETAILED DESCRIPTION

Embodiments will now be discussed with reference to the accompanying figures, which depict one or more exemplary embodiments. Embodiments may be implemented in many different forms and should not be construed as limited to the embodiments set forth herein, shown in the figures, or described below. Rather, these exemplary embodiments are provided to allow a complete disclosure that conveys the principles of the invention, as set forth in the claims, to those of skill in the art.

Term Definitions

As used herein, the term "user" or "application user" may include, but is not limited to, an individual who has been granted access to a digital application and/or website on a computing device, wherein the user or application user utilizes the application and/or website.

As used herein the term "physiological data," "user physiological data," or "user activity physiological data," may include data associated with a user's body, such as, but not limited to, heart rate, respiratory rate, blood pressure, blood oxygen level, skin and/or body temperature, sweat output, muscle activity, sleep quality, and calorie burn, which may be collected from a variety of sensors, devices, and/or machines associated with the user while a user is performing a physical activity.

As used herein, the term "motion data," "user motion data," or "user activity motion data" may include data associated with the movement of a user's body, such as, but not limited to speed, acceleration, velocity, revolutions per minute, changes in altitude of a user's body and/or individual body parts, changes in location and/or direction of a user's body and/or individual body parts, and changes in a user's geographical location, which may be collected from a variety of sensors, devices, or machines associated with the user while a user is performing a physical activity.

As used herein, the term "input data," or "user input data," may include, but is not limited to, data received and/or collected from a user, for example, through a user interface of an application. User input data may include user profile data, such as name age, gender, weight, fitness level and/or fitness goals. User input data may include activity event data defining or describing various activity attributes, such as but not limited to activity name, duration of activity, activity intensity, number of participants, as well as various performance metrics. User input data may further include user time data such as, but not limited to time, date, season, period, as well as user preferences regarding how the time should be divided when generating the activity data representations. User input data may further include user lifestyle data, such as user mood, user mindset, and/or user sleep, nutrition, exercise and/or social habits. User input data may further include user preference data, such as, but not limited to, a preference for a type of data representation to generate.

As used herein, the term "pre-activity user input data" may include data received and/or collected from a user prior to initiation of a physical activity, while the term "post-activity user input data" may include data received and/or collected from a user after completion of a physical activity.

As used herein, the term "model," "mathematical model," or "data representation mathematical model" may include a mathematical based system, such as a mathematical algorithm, function, and/or formula, that takes in one or more data inputs and processes the data inputs in a predefined manner to transform the data inputs into one or more data outputs, wherein the data outputs are transformed representations of the data inputs.

As used herein, the term "representation," or "data representation," may include visual, audio, textual, and/or physical representations of raw user data, which may be generated by inputting the raw user data into one or more mathematical models to transform the raw data into one or more representations of the raw user data.

As used herein, the term "visual representation," or "visual data representation," may include, but is not limited to, visual representations, such as still images, videos, or animations.

As used herein, the term "audio representation," or "audio data representation," may include, but is not limited to audio representations, such as songs, musical scores, spoken word recordings, sound effects and/or ringtones.

As used herein, the term "textual representation," or "textual data representation," may include, but is not limited to textual representations, such as poetry and/or prose.

As used herein, the term "physical representation," or "physical data representation," may include, but is not limited to physical representations, such as 3d physical models, sculptures, and/or figurines.

As used herein, the term "parameter," "data representation parameter," or "user activity data representation parameters" may include data that is used to define various data representations. For example, a visual and/or physical data representation may be defined by parameters such as, but not limited to, shape, line, curve, pattern, texture, material, color, tone, contrast, lighting, viewpoint, depth, balance, and/or use of space. An audio data representation may be defined by parameters such as, but not limited to, melody, harmony, rhythm, tempo, texture, dynamics, pitch, form, and timbre. A textual data representation may be defined by parameters such as, but not limited to, theme, mood, imagery, character, setting, word choice, repetition, and rhyme.

System

Embodiments of the present disclosure provide a technical solution to the technical problem of transforming health and exercise-related data received and/or collected from individuals into one or more individualized, unique and/or artistic data representations to inspire and motivate individuals to maintain healthy lifestyles while engaging in activities that foster the growth and development of social connections.

As noted above, in the disclosed embodiments, the system and method disclosed herein uses various technological methods to collect user data and user activity data from one or more users of an application and the user data and user activity data is utilized to generate a variety of visual, audio, textual, and/or physical data representations, which may be provided to the one or more users either dynamically in real-time during an activity, such as a physical exercise activity, or may be provided to the one or more users after the completion of one or more activities. The goal is to help motivate individuals to maintain healthy exercise, nutritional, and social routines by dynamically generating individualized and/or artistic data representations that are unique to one or more activity sessions of a particular user and/or particular group of users.

FIG. 1 is an overview 100 of a method and system for transforming user data and user activity data into various data representations, in accordance with one embodiment.

In the simplified overview of FIG. 1, user data and user activity data may include physiological and motion data 104 and/or user input data 106, which is received and/or collected from user 102 via a variety of mechanisms, as will be discussed in further detail below. In various embodiments, physiological and motion data 104 may include data associated with a user and a user's activities such as, but not limited to, heart rate, respiratory rate, blood pressure, blood oxygen level, skin and/or body temperature, sweat output, muscle activity, sleep quality, calorie burn, speed, acceleration, velocity, revolutions per minute, changes in altitude of a user's body and/or individual body parts, changes in location and/or direction of a user's body and/or individual body parts, and changes in a user's geographical location, which may be collected from various sensors, devices, or machines associated with the user. In various embodiments, user input data 106 may include, but is not limited to, data received and/or collected from a user, for example, through a user interface of an application. User input data 106 may include data such as user profile data, user activity event data, user time data, user lifestyle data, and/or user preference data, all of which will be discussed in additional detail below. In one embodiment, once the physiological and motion data 104 and/or user input data 106 is collected, it is provided to one or more mathematical models 108. In one embodiment, mathematical models 108 are selected based, at least in part, on physiological and motion data 104 and/or user input data 106. In one embodiment, the mathematical models 108 take raw physiological and motion data 104 and/or raw user input data 106 as inputs and process the raw data to transform the input into one or more values, such as, but not limited to, numerical values, which can then be provided to parameter mapping module 110. In one embodiment, parameter mapping module 110 takes the outputs from mathematical models 108 and maps the outputs to a variety of data representation parameters in order to define and/or generate data representations such as visual data representation 112, audio data representation 114, textual data representation 116, and physical data representation 118, all of which will be discussed in additional detail below.

Figure 2A:
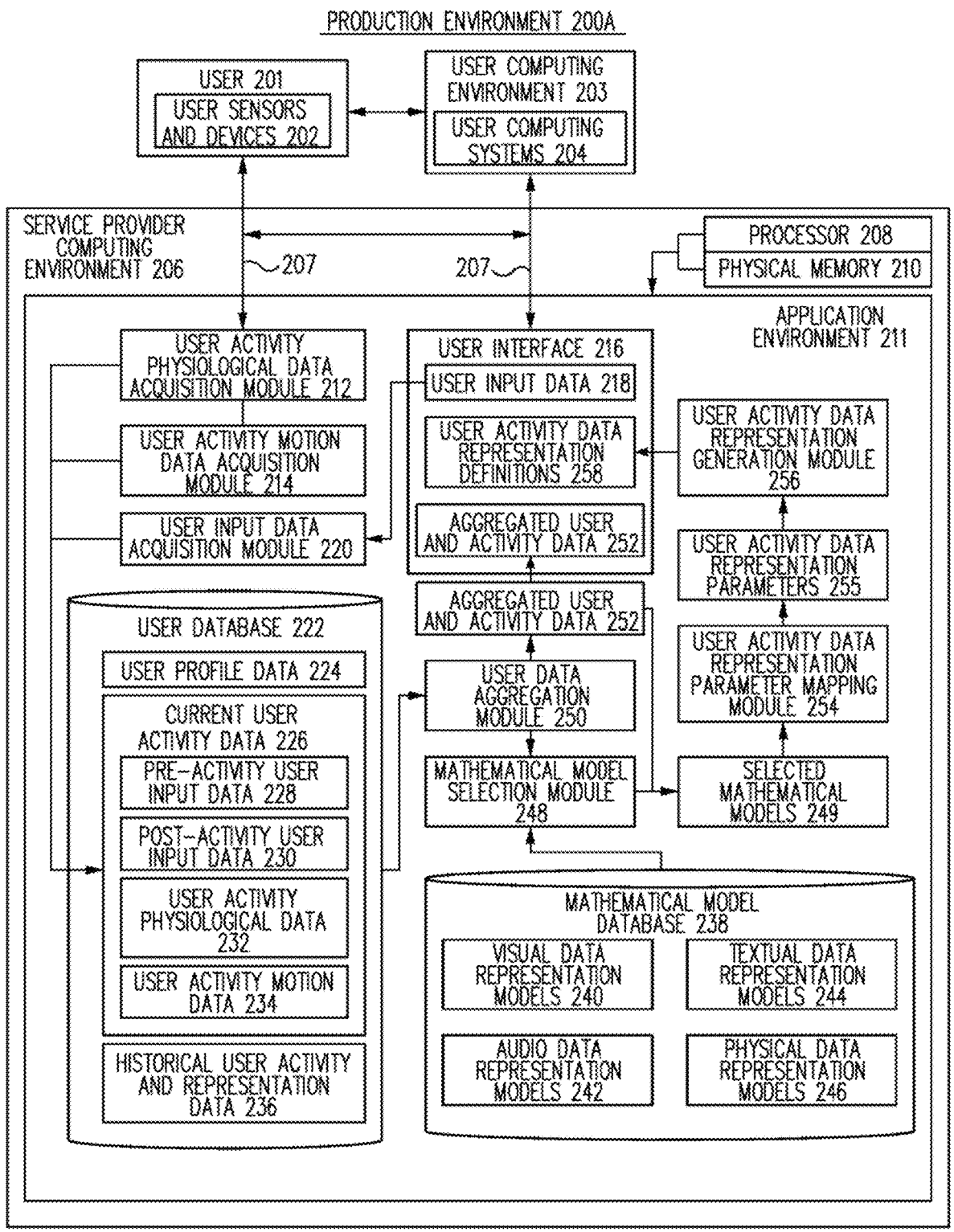
FIG. 2A is a diagram of a production environment for transforming user data and user activity data into various data representations, in accordance with one embodiment.

FIG. 2A is a diagram of a production environment 200A for transforming user data and user activity data into various data representations, in accordance with one embodiment.

In one embodiment, production environment 200A includes user 201, user sensors and devices 202, user computing environment 203, and user computing systems 204. In one embodiment, production environment 200A also includes service provider computing environment 206, one or more communications channels 207, and application environment 211. In one embodiment, service provider computing environment 206 further includes processor 208 and physical memory 210, which together coordinate the operation and interaction between the various data elements and process modules. In one embodiment, communications channels 207 facilitate collection of user input data 218 through user interface 216, and also facilitate collection of user activity physiological data 232 and user activity motion data 234, which may be received and/or collected from user sensors and devices 202. Each of the above listed elements will be discussed in further detail below.

In various embodiments, application environment 211 includes user database 222 and mathematical model database 238. In one embodiment, user database 222 includes user profile data 224, current user activity data 226, and historical user activity and representation data 236. In one embodiment current user activity data 226 further includes pre-activity user input data 228, post-activity user input data 230, user activity physiological data 232 and user activity motion data 234.

In one embodiment, mathematical model database 238 includes visual data representation models 240, audio data representation models 242, textual data representation models 244, and physical data representation models 246. In one embodiment, application environment 211 further includes user interface 216, which further includes user input data 218, user activity data representation definitions 258, and aggregated user and activity data 252. In one embodiment, application environment 211 further includes user activity physiological data acquisition module 212, user activity motion data acquisition module 214, and user input data acquisition module 220. In one embodiment, application environment 211 further includes user data aggregation module 250, aggregated user and activity data 252, and mathematical model selection module 248. In one embodiment application environment 211 further includes selected mathematical models 249, user activity data representation parameter mapping module 254, user activity data representation parameters 255 and user activity data representation generation module 256. In one embodiment, user activity data representation generation module 256 generates user activity data representation definitions 258, which may be utilized to provide user activity data representations to user 201 through user interface 216, which, in some embodiments, communicates with user computing systems 204 over one or more communications channels 207. Each of the above listed elements will be discussed in further detail below.

In one embodiment, user 201 is a user of an application and/or website, such as that provided by application environment 211. In one embodiment, the application is designed to facilitate collection of data associated with user 201, in order to transform the user data into unique and/or artistic visual, audio, textual and/or physical data representations, which can be generated and provided to user 201 in a digital and/or physical format. As one simplified illustrative example, user 201 may decide to participate in a physical activity, such as walking or running, and may engage with a device and/or user interface associated with the application in order to initiate collection of data associated with the activity. In one embodiment, user interface 216 of application environment 211 is provided to user 201 via one or more user computing systems 204 associated with user computing environment 203. In various embodiments, user computing systems 204 may include, but are not limited to, a desktop computing system, a mobile computing system, a virtual reality computing system, a gaming computing system, a computing system that utilizes one or more Internet of Things (IoT) devices, and/or any other type of computing system discussed herein, known at the time of filing, developed/made available after the time of filing, or any combination thereof.

FIG. 3A through FIG. 3F are examples of a user interface 216 that may be provided to user 201 and utilized for transforming user data and user activity data into various data representations, in accordance with one embodiment.

Figure 3A:
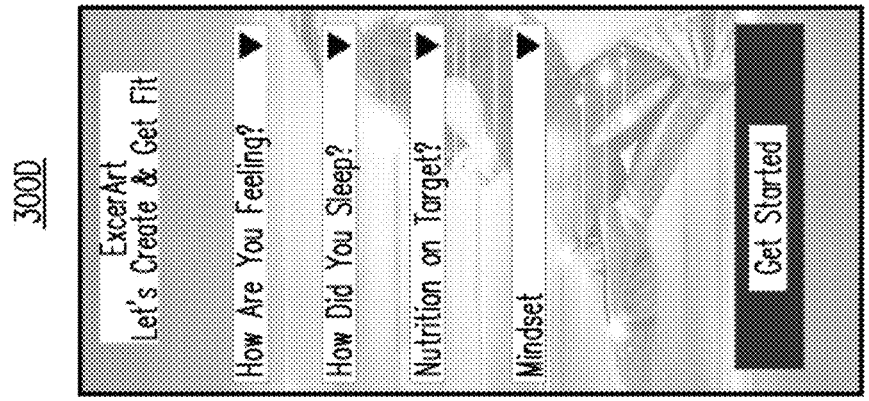
FIG. 3A through FIG. 3G are examples of a user interface that may be provided to a user and utilized for transforming user data and user activity data into various data representations, in accordance with one embodiment.
Figure 3B:
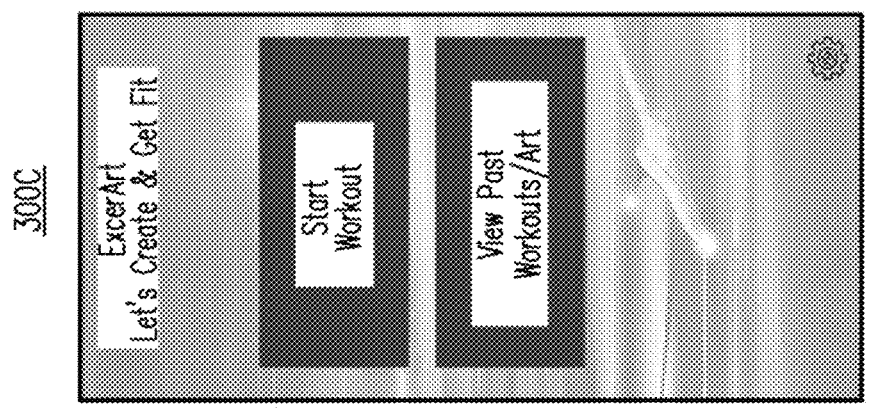
Figure 3C:
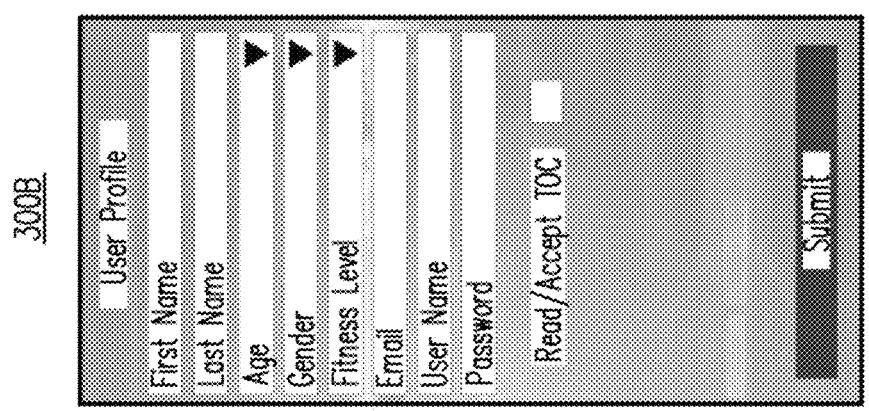

Referring now to FIG. 2A and FIG. 3A through FIG. 3F together, in one illustrative embodiment, user 201 may sign into the application environment 211 via user interface 216, and user 201 may first be presented with a welcome screen, such as welcome screen 300A of FIG. 3A. Upon selection of an option to "Get Started," user 201 may then be prompted to answer several questions prior to beginning the chosen physical activity. If it is the first time user 201 is utilizing the application, user input data 218 may be requested, which in some embodiments includes user profile data, such as name, age, gender, weight, and activity level. FIG. 3B shows an illustrative example of a user profile data collection screen 300B, in accordance with one embodiment. The user profile data may then be aggregated by user input data acquisition module 220, and the data may be stored as user profile data 224 in a data structure, such as user database 222. In one embodiment, user profile data 224 is initially stored on the device running the application, and is later transmitted to a server for processing and/or long-term storage. In some embodiments, user profile data 224 is transmitted directly to a server for processing and/or long-term storage.

In one embodiment, user database 222 may also include historical user activity and representation data 236, which may include any collected data associated with user 201's past activities, as well as any data related to past data representations generated for user 201. In the illustrative embodiment of FIG. 3C, user 201 is given an option, through user interface screen 300C, to view these past activities (e.g. past workouts) or past data representations (e.g. past artwork), or to proceed with a new activity, such as a new workout.

Figure 3D:
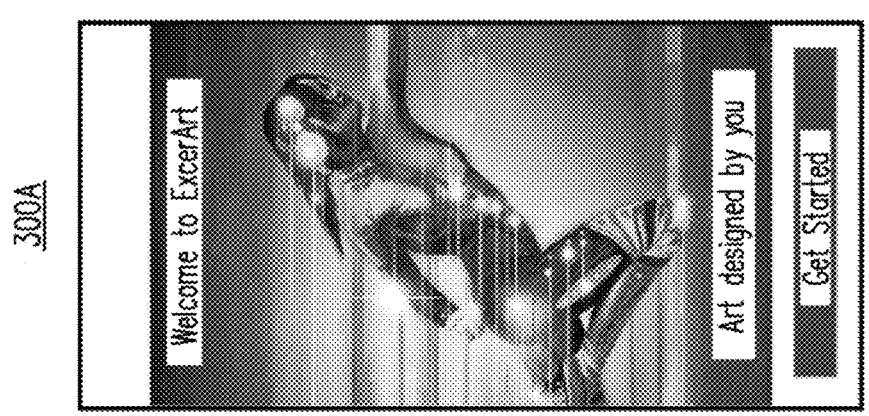

In some embodiments, prior to beginning a physical activity, additional user input data 218 may be collected by user input data acquisition module 220. For example, the user may input data related to date and time associated with the activity, data related to the lifestyle of user 201, data related to the event and/or physical activity that is to be monitored, and/or various preferences, such as preferences for the type of data transformation to perform, as will be discussed in additional detail below. In some embodiments, user input data 218 collected prior to user 201 beginning a physical activity may be collected by user input data acquisition module 220 and stored as pre-activity user input data 228 in a data structure, such as user database 222. FIG. 3D shows an illustrative example of collection of pre-activity user input data 228 through pre-activity data collection screen 300D.

Figure 3G:
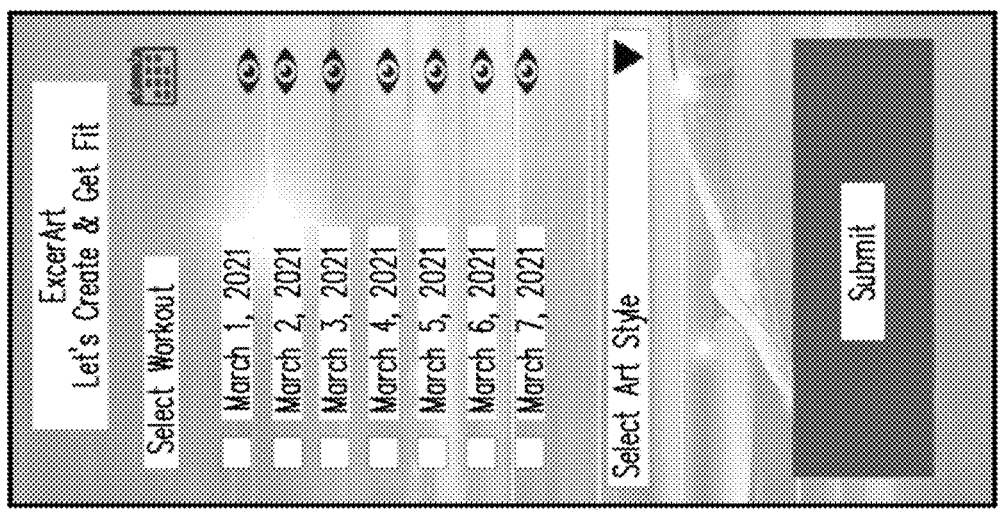
Figure 3F:
Figure 3E:
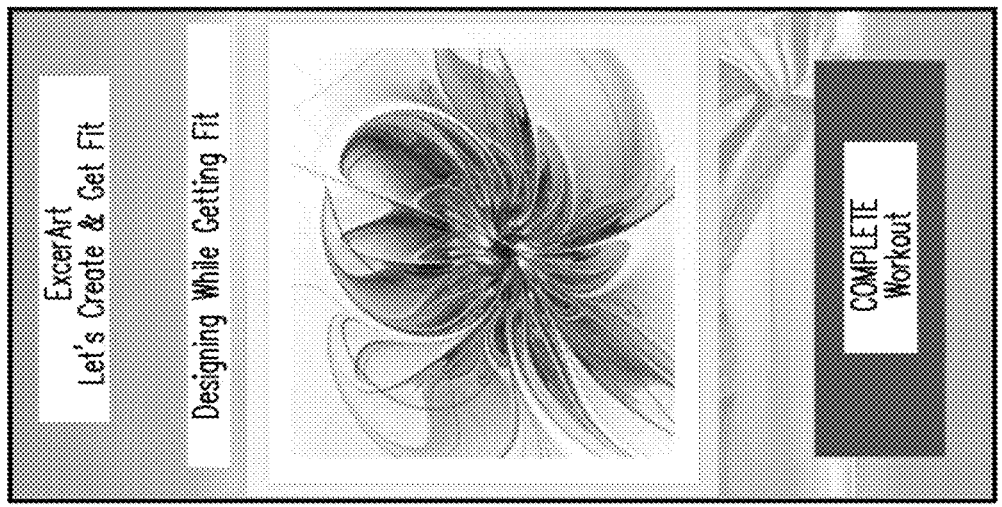

In one embodiment, once user input data acquisition module 220 has collected and stored pre-activity user input data 228, collection of physiological and motion data associated with user 201 during the physical activity may be initiated, and user 201 may be presented with one or more user interface screens, such as user interface screen 300E, shown in FIG. 3E. In one embodiment user interface screen 300E presents user 201 with an animated GIF or video showing user 201 that they are creating a data representation, such as an artistic representation, while engaging in the activity. Other embodiments of user interface screen 300E of FIG. 3E will be discussed in additional detail below.

In some embodiments, additional user input data 218, such as that described above with respect to pre-activity user input data 228, may be collected by user input data acquisition module 220 after completion of a physical activity, and may be stored as post-activity user input data 230 in a data structure, such as user database 222. FIG. 3F and FIG. 3G are screenshots of post-activity data collection screen 300F and post-activity data collection screen 300G, in accordance with one illustrative embodiment. In some embodiments, only pre-activity user input data 228 is collected. In some embodiments, only post-activity user input data 230 is collected. In some embodiments, both pre-activity user input data 228 and post-activity user input data 230 are collected. In some embodiments, neither pre-activity user input data 228 nor post-activity user input data 230 is collected, and a variety of default settings may be utilized to transform data received from user sensors and devices 202 into one or more data representations.

In various embodiments, once user 201 has begun the physical activity, user activity physiological data acquisition module 212 collects user activity physiological data 232 from user 201 and user activity motion data acquisition module 214 collects user activity motion data 234 from user 201. In one embodiment, user activity physiological data 232 and user activity motion data 234 are collected from user 201 by user activity physiological data acquisition module 212 and user activity motion data acquisition module 214 via one or more user sensors and devices 202 and the data is stored locally within user sensors and devices 202, and/or is transmitted to a server over one or more communications channels 207. In one embodiment, one or more user sensors and devices 202 are attached to or in close proximity to user 201. In one embodiment, user sensors and devices 202 may include sensors and devices such as, but not limited to, a smart phone, a smart watch, a tablet, a laptop computing system, a desktop computing system, an Internet of Things (IoT) device, and/or computing systems and sensors that may be incorporated into exercise equipment. In various embodiments, user sensors and devices 202 may include sensors and devices such as accelerometers, gyroscopes, global positioning system (GPS) devices, heart rate monitors, blood pressure monitors, blood oxygen level monitors, sleep quality monitors, epidermal sensors, electromyograph devices, blood testing devices, and/or any other devices capable of collecting user physiological and/or motion data, as discussed herein, known at the time of filing, and/or developed/made available after the time of filing. In various embodiments, user activity physiological data 232 may include data such as, but not limited to, user 201's heart rate, respiratory rate, blood pressure, blood oxygen level, skin and/or body temperature, sweat output, muscle activity, sleep quality, and/or calorie burn. In various embodiments user activity motion data 234 may include data such as, but not limited to, user 201's speed, acceleration, velocity, revolutions per minute, changes in altitude of user 201's body and/or user 201's individual body parts, changes in location and/or direction of user 201's body and/or user 201's individual body parts and/or changes in user 201's geographical location.

In one embodiment, after user 201 has indicated completion of an activity, such as through user interface screen 300E of FIG. 3E, the collected user activity physiological data 232 and user activity motion data 234 may be stored in a data structure, such as user database 222 for further processing. In one embodiment, user activity physiological data 232 and user activity motion data 234 is collected by user sensors and devices 202 during the activity, but is not transmitted to the respective data acquisition modules until after the activity is completed. In this situation, the resulting data representations may be generated and provided to user 201 after completion of the activity. In other embodiments, user activity physiological data 232 and user activity motion data 234 are transmitted to the respective data acquisition modules in real-time, or near real-time. In the case of real-time data transmission, the resulting data representations may then be provided to user 201 in real-time, for instance, through a user interface screen, such as user interface screen 300E of FIG. 3E, such that user 201 can watch the data representation change and/or grow as it is being generated, as will be discussed in additional detail below. It should be noted herein that the above examples of user interface screenshots are given for illustrative purposes only, and are not intended to limit the scope of the invention as disclosed and as claimed herein. One of ordinary skill in the art will readily appreciate that many other styles, designs, and layouts of user interface elements may be utilized to achieve the same effect.

Figure 4B:
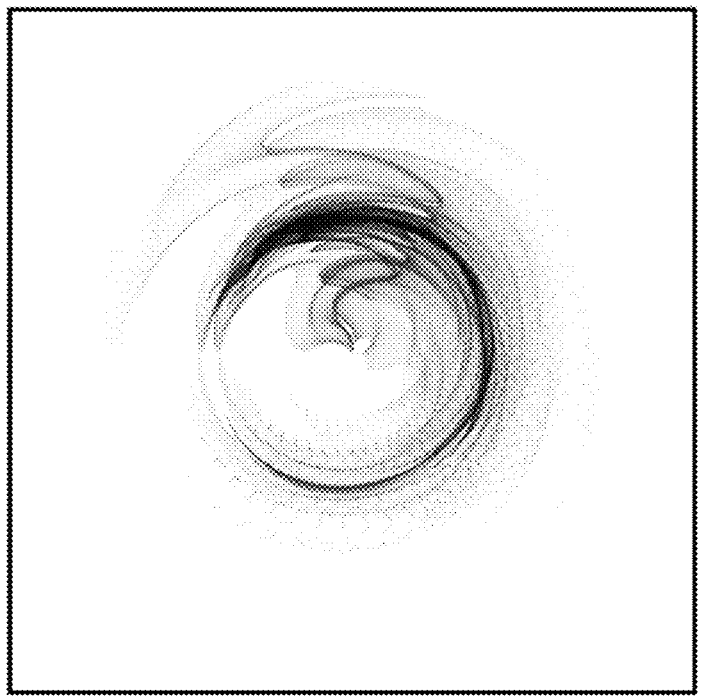
FIG. 4B is an example of a visual data representation generated from user data and user activity data obtained while a user is running, in accordance with one embodiment.
Figure 4A:
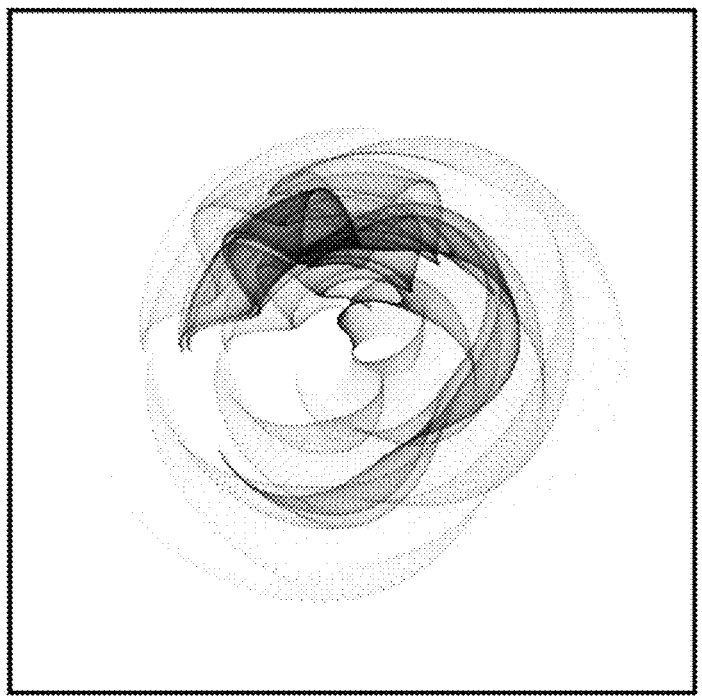
FIG. 4A is an example of a visual data representation generated from user data and user activity data obtained while a user is walking, in accordance with one embodiment.

FIG. 4A is an example of a visual data representation 400A generated from user data and user activity data obtained while a user is walking, in accordance with one embodiment.

FIG. 4B is an example of a visual data representation 400B generated from user data and user activity data obtained while a user is running, in accordance with one embodiment.

As can be seen in the simplified illustrative examples of FIG. 4A and FIG. 4B, data obtained while a user is walking results in a different visual data representation than data obtained while a user is running. Further, the visual data representations 400A and 400B are likely to change over time, and will be highly individualized to the specific user for a specific activity session. For example, user 201 may start out one activity session walking slowly, and then ramp up to a slow jog, before slowing down to a walk again. User 201 may sprint for the duration of a second activity session, and may alternate between walking, jogging, and running during a third activity session, and each of these activity sessions will result in a unique visual data representation, which is generated by utilizing the highly individualized user data and user activity data that is collected for that activity session. The process and mechanisms for generating the data representations, such as those depicted in FIG. 4A and FIG. 4B will be discussed in additional detail below.

Figure 2B:
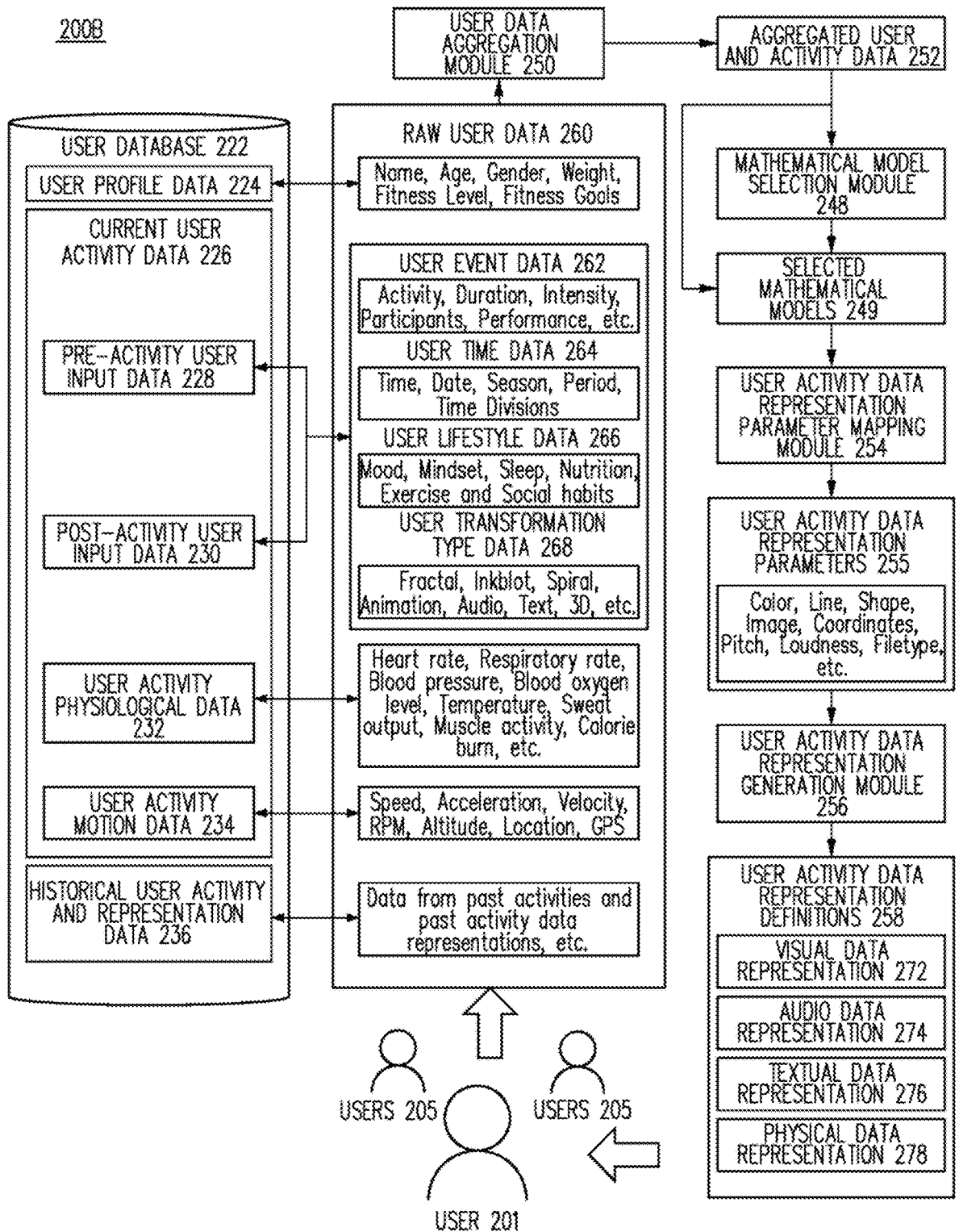
FIG. 2B is a diagram depicting examples of user data and user activity data which may be aggregated for transformation into various data representations, in accordance with one embodiment.

FIG. 2B is a diagram 200B depicting examples of user data and user activity data which may be aggregated for transformation into various data representations, in accordance with one embodiment.

As discussed above, a data structure, such as user database 222 may include various types of data. For example, in one embodiment, user database 222 may include user profile data 224, current user activity data 226, and historical user activity and representation data 236. Current user activity data 226 may further include pre-activity user input data 228, post-activity user input data 230, user activity physiological data 232, and user activity motion data 234. All of this data combined is represented in FIG. 2B as raw user data 260, which is collected from user 201 via the mechanisms discussed above in relation to FIG. 2A. It should be noted here that the particular nomenclature used for classification of raw user data 260 depicted in FIG. 2B is given for illustrative purposes only, and is not meant to limit the scope of the invention as disclosed and claimed herein.

In various embodiments, some of raw user data 260 can be classified as objective data, which can typically best be measured by sensors and/or devices associated with user 201, some of raw user data 260 can be classified as subjective data, which can typically best be measured by collecting user input data directly from user 201. In some embodiments, raw user data 260 may have both subjective and objective components. For example, in one embodiment, activity intensity may be subjectively determined by user 201, and the subjectively perceived activity intensity may be taken into account, and/or activity intensity may be objectively calculated based on user activity physiological data 232 and/or user activity motion data 234, such as heart rate and acceleration. In various embodiments, raw user data 260 may be collected from manually entered user input data and/or raw user data 260 may be obtained automatically via any number of sensors and/or devices. In some embodiments, raw user data 260 may be obtained by other means, such as by performing lab tests on a user 201, for example, a user may have blood work done, and the blood work may be analyzed to obtain health and nutrition-related data from user 201.

As shown in FIG. 2B, in various embodiments, raw user data 260 may include user profile data 224, which, in the illustrative embodiment of FIG. 2B represents user data such as, but not limited to, the user's name, age, gender, weight, fitness level, and fitness goals. In various embodiments, pre-activity user input data 228 may be collected prior to the start of an activity session and/or post-activity user input data 230 may be collected after the completion of an activity session. In some instances, user input data may be collected during the activity session, however, more typically, the user will be engaged with the activity session and so user data, such as user activity physiological data 232 and user activity motion data 234 would be collected automatically from one or more sensors and/or devices associated with user 201, without the need for user 201 to manually input the data.

In the illustrative embodiment of FIG. 2B, some examples of pre-activity user input data 228, and post-activity user input data 230 include user event data 262, user time data 264, user lifestyle data 266, and user transformation type data 268. In various embodiments, user event data 262 may include data related to activity events/sessions associated with user 201. For example, user event data 262 may include data such as, but not limited to, the type of activity user 201 engaged in, the duration of the activity user 201 engaged in, the intensity of the activity user 201 engaged in, the number of participants that engaged in the activity, as well as a variety of performance metrics related to the activity.

In various embodiments, user time data 264 may include data such as the time and date of the physical activity, the season during which the physical activity event took place, and/or user 201 may specify periods of time, or divisions of time, which may be utilized to determine what data is to be used for generating a data representation. For example, user 201 may wish for the data representation to utilize data only from a single activity session and/or from a collection of activity sessions. User 201 may instead wish for the data representation to utilize data from a single week, month or quarter of the year, or data from the whole year, and/or any other time period specified by user 201. Additionally, the data representations generated by the method and system disclosed herein may change depending on factors such as the time of day, or the season of the year. Thus, including time as a data dimension enables the user data and user activity data to be analyzed with any custom time division desired by user 201.

FIG. 5A through FIG. 5D are examples of visual data representations 500A through 500D created from user data and user activity data obtained from a user over the course of a year, in accordance with one embodiment.

Referring to FIG. 2B and FIG. 5A through FIG. 5G together, FIG. 5A through FIG. 5D illustrate one example of the way in which the method and system disclosed herein may utilize user time data 264, along with other elements of raw user data 260, to generate various data representations. In the illustrative example of FIG. 5A through FIG. 5D, one or more mathematical models are selected to generate one or more visual data representations that display a user's exercise habits throughout the course of a year. Raw user data is provided as inputs to the one or mathematical models, as will be discussed in additional detail below. In one embodiment, the input may come in the form of an array of integers with a length of 1 to 365, with each integer in the array representing the number of minutes a user was active on a particular day during the specified year. In one embodiment, the activity duration for a particular day may be measured by sensor and device data, in other embodiments, the activity duration may be provided manually by user input data. In one embodiment, the length of the array may be determined by how many days have passed since the user's year began, and the array may expand to include new data as the year progresses.

The visual data representations shown in the illustrative embodiments of FIG. 5A through FIG. 5D consist of a ring, which represents a full year, within which there is an arc, which marks the number of elapsed days since the user's year began. If the user was active on a particular day, a tree representation is displayed, whose position corresponds to that particular day, and whose size corresponds to the number of minutes the person was active that day. In one embodiment, the color and exact shape of the tree may be determined by random inputs, while in other embodiments, the color and exact shape of the tree may be determined by additional user data and user activity data, such as, but not limited to, the season of the year during which the activity took place, the time of day during which the activity took place, the mood of the user at the time the activity took place and/or the intensity of the activity session, each of which may either be measured objectively by data collected automatically from sensors and/or devices, or measured subjectively by collection of manually entered user input data.

Figure 5A:
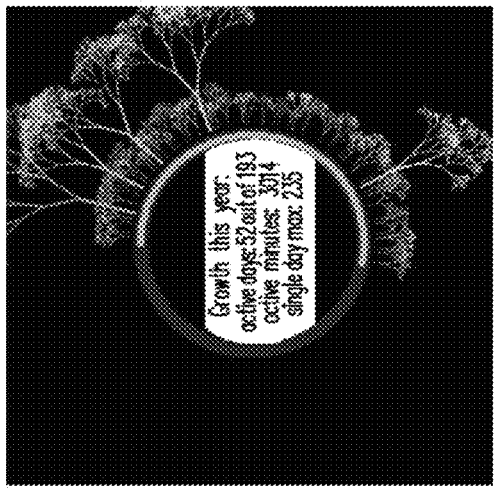
FIG. 5A through FIG. 5D are examples of visual data representations created from user data and user activity data obtained from a user over the course of a year, in accordance with one embodiment.
Figure 5B:
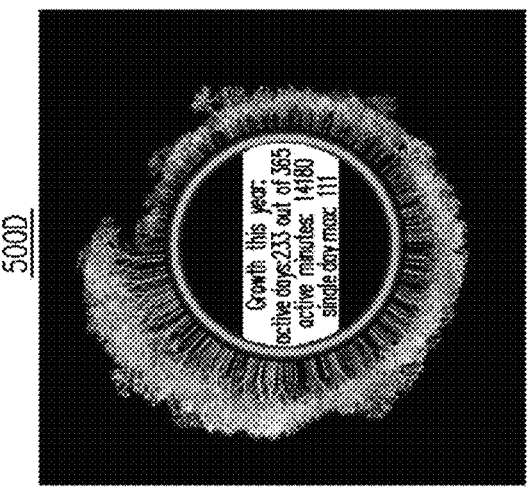
Figure 5C:
Figure 5D:
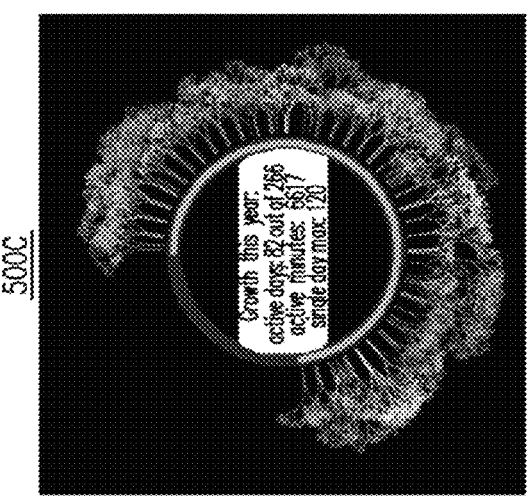
Figure 6B:
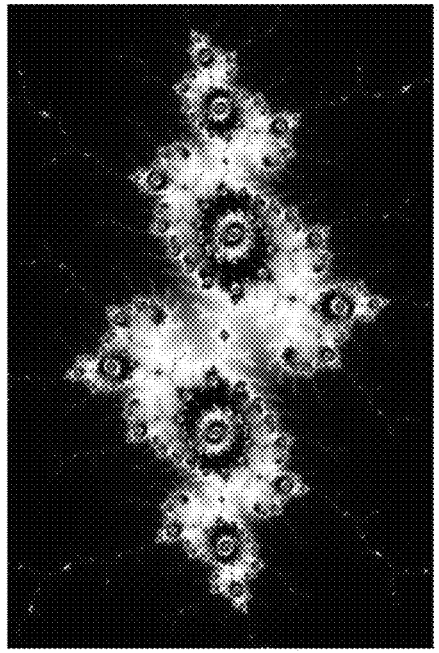
FIG. 6A through FIG. 6L are examples of differing styles of visual data representations created from user data and user activity data obtained from a user, in accordance with one embodiment.
Figure 6D:
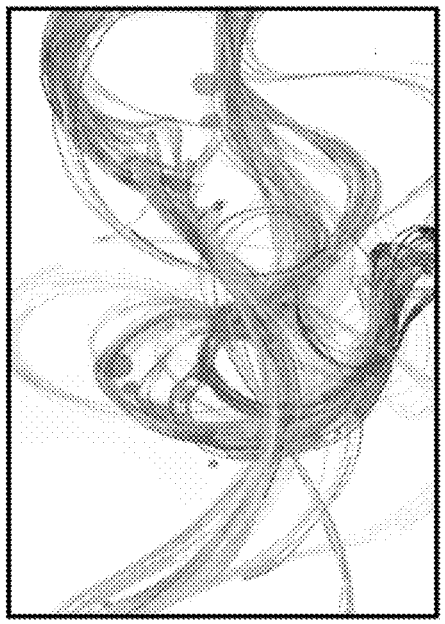
Figure 6A:
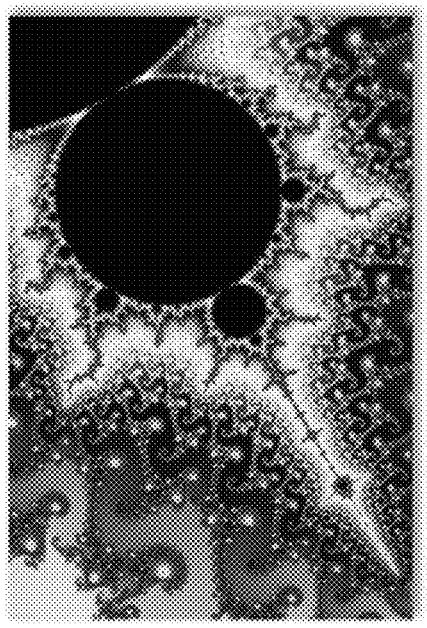
Figure 6C:
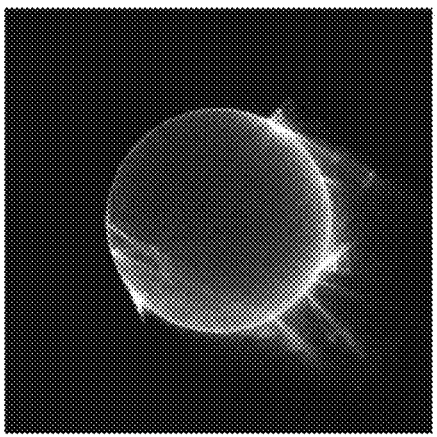
Figure 6F:
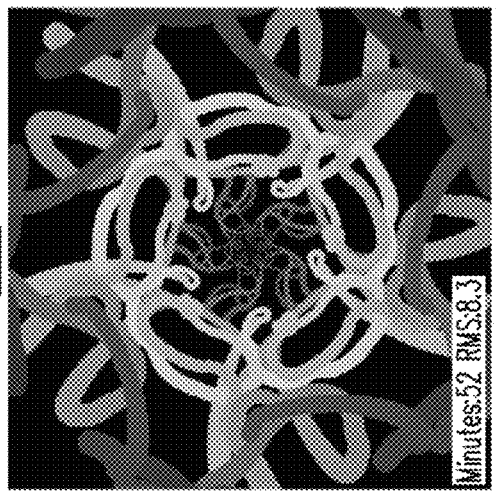
Figure 6H:
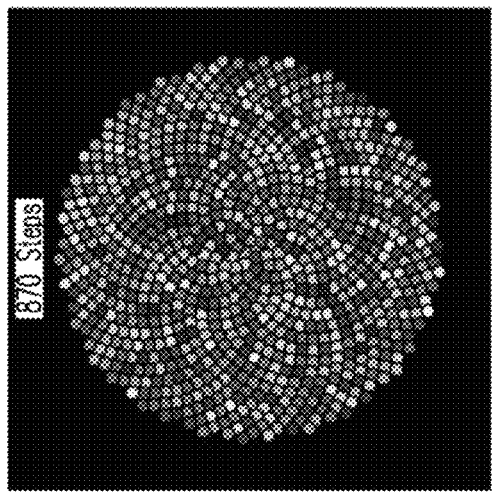
Figure 6E:
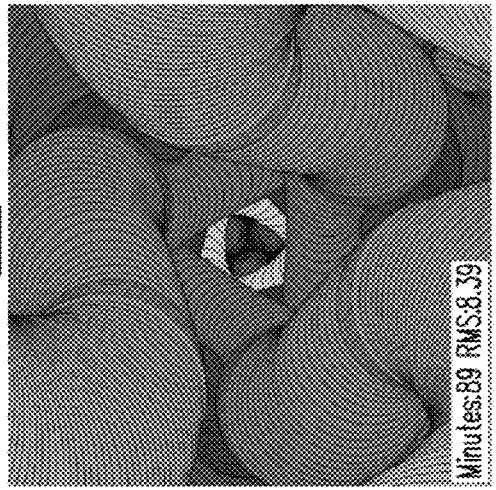
Figure 6G:
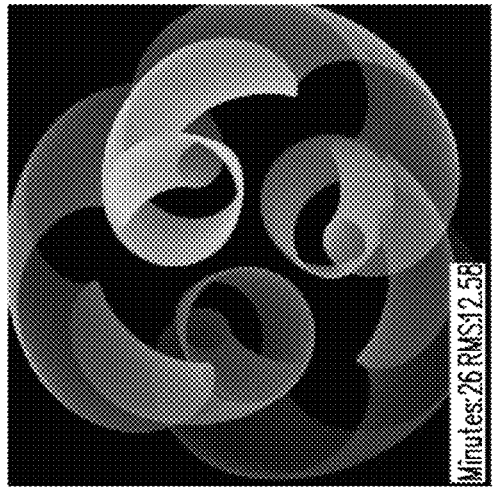
Figure 6J:
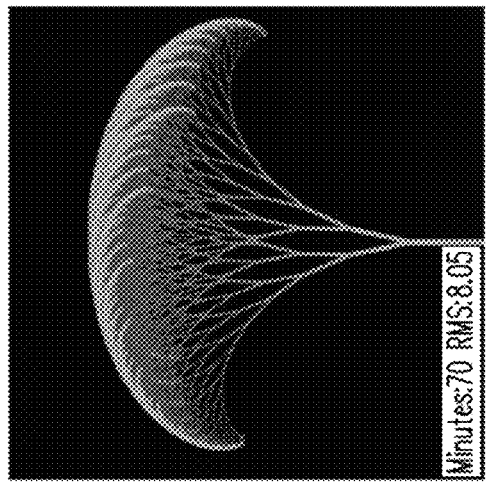
Figure 6L:
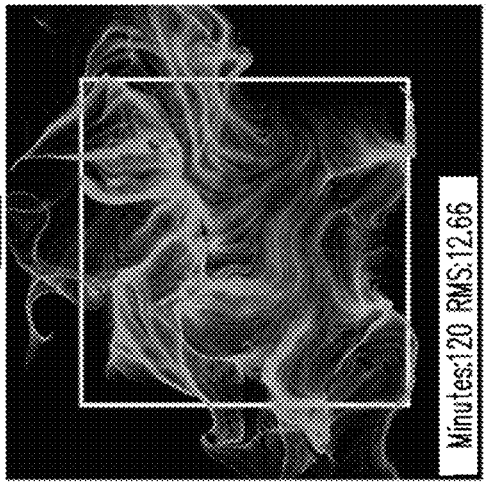
Figure 6I:
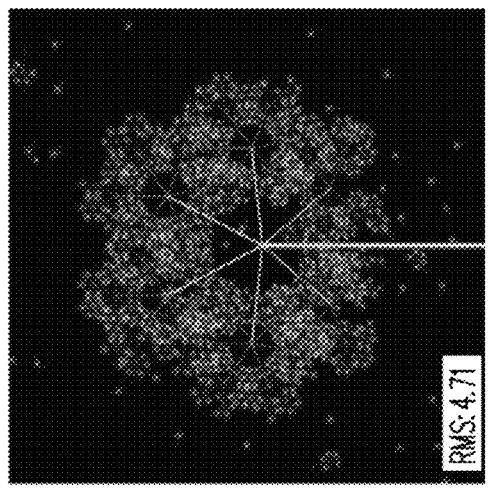
Figure 6K:
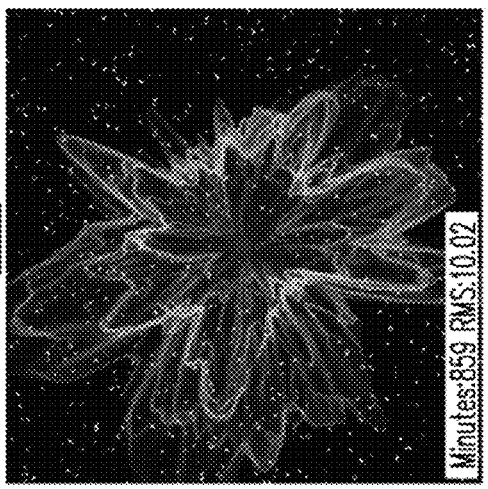
Figure 7A:
FIG. 7A through FIG. 7F are examples of an animated visual data representation created from user data and user activity data obtained from a user, in accordance with one embodiment.
Figure 7B:
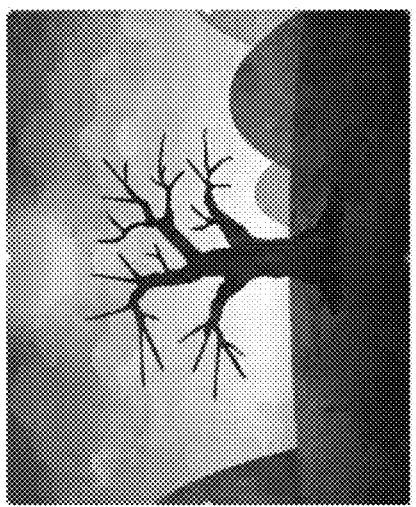
Figure 7C:
Figure 7D:
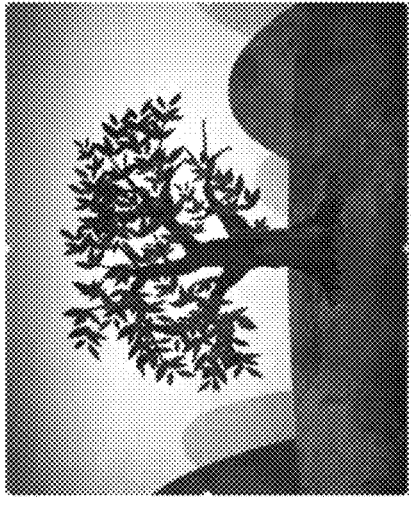
Figure 7E:
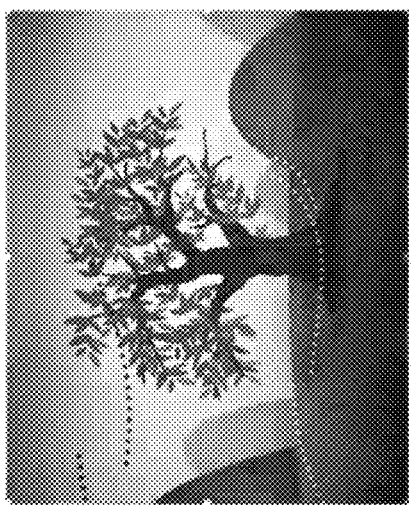
Figure 7F:
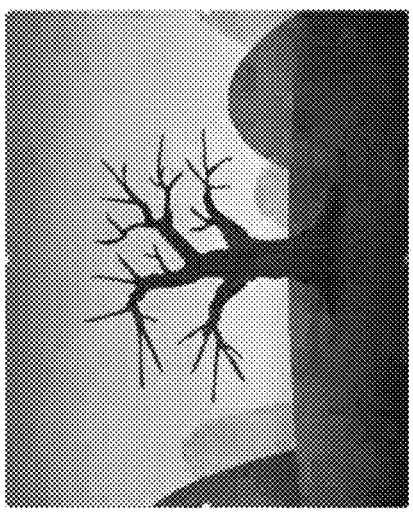

Data representation 500A of FIG. 5A is a visual data representation of user data and user activity data, collected over the first quarter of a year, in accordance with one embodiment, and is a representation of a classic "New Year's resolution scenario," in which the user began the year working out frequently for one to two hours per day, but then only exercises sporadically and for shorter durations as the year progresses. Data representation 500B of FIG. 5B is a visual data representation of user data and user activity data, in accordance with one embodiment, collected over the first half of a year, which represents a user who regularly works out on Tuesdays and Thursdays, and occasionally takes long hikes on weekends. Data representation 500C of FIG. 5C is a visual data representation of user data and user activity data, in accordance with one embodiment, collected over the first three quarters of a year, which represents a user who usually does long workouts each weekend, and occasionally does shorter workouts during the week as well. Data representation 500D of FIG. 5D is a visual data representation of user data and user activity data, in accordance with one embodiment, collected over an entire year, which represents a user who began the year exercising for short durations, and gradually increased the length of the workouts throughout the entire course of the year. As noted above, the examples of FIG. 5A through FIG. 5D are given for illustrative purposes only, and are not intended to limit the scope of the invention as disclosed and as claimed herein. Hundreds or thousands of possible data representations are contemplated by the disclosure set forth herein, and each may utilize a unique mathematical model to transform the raw user input into a desired data representation, as will be discussed in additional detail below.

Returning now to FIG. 2B, in various embodiments, user lifestyle data 266 may include user input data received and/or collected from user 201 relating to user mood, user mindset, user exercise habits, user nutrition/eating habits, user sleep habits, and/or user social habits. For example, a data representation of physical activity for a particular day might be different depending on various factors, such as, but not limited to, whether user 201 reported a particular mood, reported that they did or did not sleep and/or eat well that day, and/or whether user 201 engaged in any positive, negative and/or neutral social activities during the day. In various embodiments, user lifestyle data 266 may be mapped to various data representation parameters, such as, but not limited to color, line, and shape of the data representation, as will be discussed in additional detail below.

In various embodiments, user transformation type data 268 may include user preference data related to the type of data representation that user 201 wishes to transform the user data and user activity data into. For example, user 201 may choose to have their data transformed into a visual data representation, an audio data representation, a textual data representation, and/or a physical data representation. User 201 may choose to have any combination of data representation types generated, such as a visual data representation that also includes audio elements. Within each type of data representation, there are additional types of preferences that can be selected by user 201. For example, user 201 can choose to have a visual representation in a particular style, such as, but not limited to, fractal, spiral, tree, circles, smoke, inkblot, or animated styles.

FIG. 6A through FIG. 6L are examples of differing styles utilized for visual data representations 600A through 600L, which may be generated from user data and user activity data obtained from a user, in accordance with one embodiment.

Referring to FIG. 2B and FIG. 6A through FIG. 6L together, FIG. 6A through FIG. 6L are a few examples of differing types of visual data representations 600A through 600L, which may be created from raw user data 260, which has been received and/or collected from a user, such as user 201. In various embodiments, the type and/or style of the data representation may be determined by user preference data, such as user transformation type data 268, may be determined randomly and/or may be determined by other elements of raw user data 260, such as, but not limited to, activity type, activity intensity, user mood, user mindset, a user's geographical location, and/or the season of the year during which the activity takes place. The specific data representation parameters, such as, but not limited to color, line, and shape of the data representation may be determined randomly, or may be determined by mapping any number of raw user data 260 elements based on the output of one or more selected mathematical models, as will be discussed in further detail below.

FIG. 7A through FIG. 7F are examples of an animated visual data representation created from user data and user activity data obtained from a user, in accordance with one embodiment.

Referring to FIG. 2B and FIG. 7A through FIG. 7D together, FIG. 7A through FIG. 7D are a few examples of frames 700A through 700F of an animated visual data representation, which may be created from raw user data 260 received and/or collected from a user, such as user 201. In various embodiments, the type and/or style of the animated visual data representation may be determined by user preference data, such as user transformation type data 268, may be determined randomly, and/or may be determined by other elements of raw user data 260, such as, but not limited to, activity type, activity intensity, user mood, user mindset, a user's geographical location, and/or the season of the year during which the activity takes place. The specific data representation parameters, such as, but not limited to color, line, and shape of the data representation may be determined randomly, or may be determined by mapping any number of raw user data 260 elements based on the output of one or more selected mathematical models, as will be discussed in further detail below. Additional parameters of an animated visual data representation may also be determined by raw user data 260. For example, the animated visual data representation in FIG. 7A through FIG. 7F depicts a tree in various stages of bloom over the course of several seasons of a year. During a single activity session, the animation speed may be dependent on the speed of user 201 during a physical activity and/or the intensity of the activity. For instance, the frames of the animated visual data representation may change more quickly or more frequently as user 201 increases speed and/or intensity of physical activity. In other embodiments, the animation may play out over the course of a longer period of time, such as several seasons of the year, and the user may be encouraged to keep pace of activity up with the changing of the seasons. As noted above, the above example is given for illustrative purposes only. One of ordinary skill in the art will recognize that any number of animations or animation styles may be utilized as an animated visual data representation, and the resulting output may be based on any number of variables represented by raw user data 260.

Figure 8B:
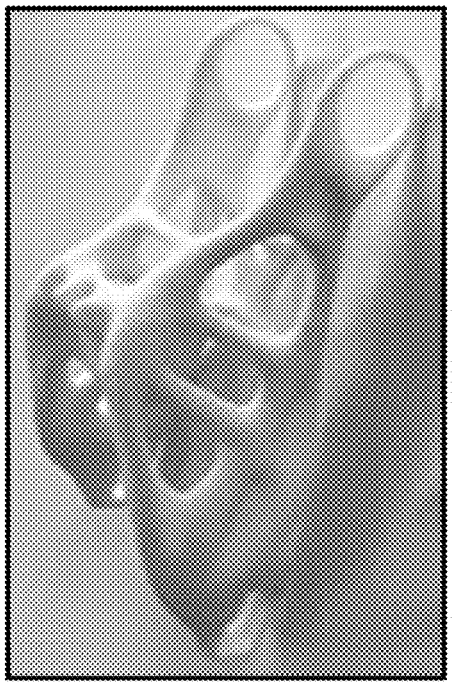
FIG. 8A and FIG. 8B are examples of physical data representations created from user data and user activity data obtained from a user, in accordance with one embodiment.
Figure 8A:
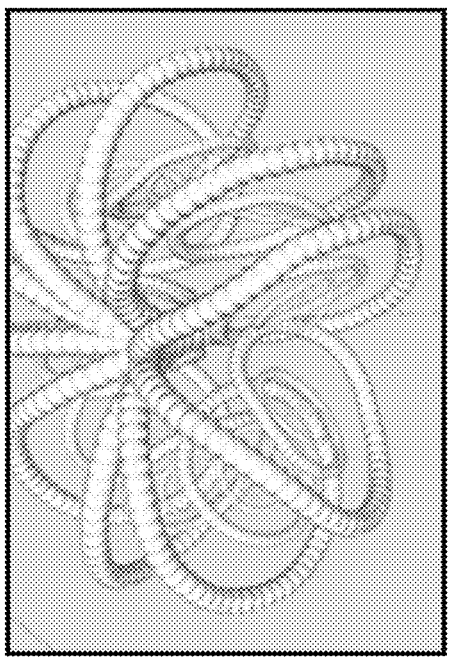

FIG. 8A and FIG. 8B are examples of physical data representations 800A and 800B created from user data and user activity data obtained from a user, in accordance with one embodiment.

As noted above, various mathematical models can be selected to transform raw user data 260 into a variety of physical representations through mapping the output of the mathematical models to various data representation parameters, as will be discussed in additional detail below. In various embodiments, physical data representation parameters may include parameters such as, but not limited to, shape, line, curve, pattern, texture, material, color, tone, contrast, and depth. Physical data representation 800A is an illustrative example of a digital representation of a physical 3D model, such as one that could be provided for manufacture to a 3D printer, or other similar machine. Physical data representation 800B is an illustrative example of an actual physical 3D model, sculpture, or figurine, as might be the result of providing a digital representation of a physical 3D model to a 3D printer in order to generate an actual physical 3D model, sculpture, or figurine. As one illustrative example, a user may decide to participate in a race, and a physical data representation may be generated that maps the shape of a figurine to a geographical route that the user took during the race. Elements of the physical data representation, such as, but not limited to color and/or material could be mapped to raw user data, such as, but not limited to, activity intensity and/or user mood. At the conclusion of the race, the resulting physical data representation could be generated and provided to a user as a trophy, reward, and/or as a memento of accomplishment for completion of the race.

Referring back to FIG. 2B, as noted above, in various embodiments, raw user data 260 further includes user activity physiological data 232 such as, but not limited to, user 201's heart rate, respiratory rate, blood pressure, blood oxygen level, skin and/or body temperature, sweat output, muscle activity, sleep quality, and calorie burn. In various embodiments raw user data 260 further includes user activity motion data 234 such as, but not limited to, user 201's speed, acceleration, velocity, revolutions per minute, changes in altitude of user 201's body and/or individual body parts, changes in location and/or direction of user 201's body and/or individual body parts, and/or changes in user 201's geographical location. In one embodiment, raw user data 260 may also include historical user activity and representation data 236, which may include any collected data associated with user 201's past activities, as well as any data related to past data representations generated for user 201.

In some embodiments, raw user data 260 is received and/or collected only for user 201, and the resulting data representation is generated based solely on user 201's data inputs. In other embodiments, data is received and/or collected from multiple users, such as user 201 and users 205 of FIG. 2B. In the embodiments where data is collected from multiple users, the resulting data representation may be generated based on data inputs from each user and/or based on data inputs from a subset of the users.

Figure 9:
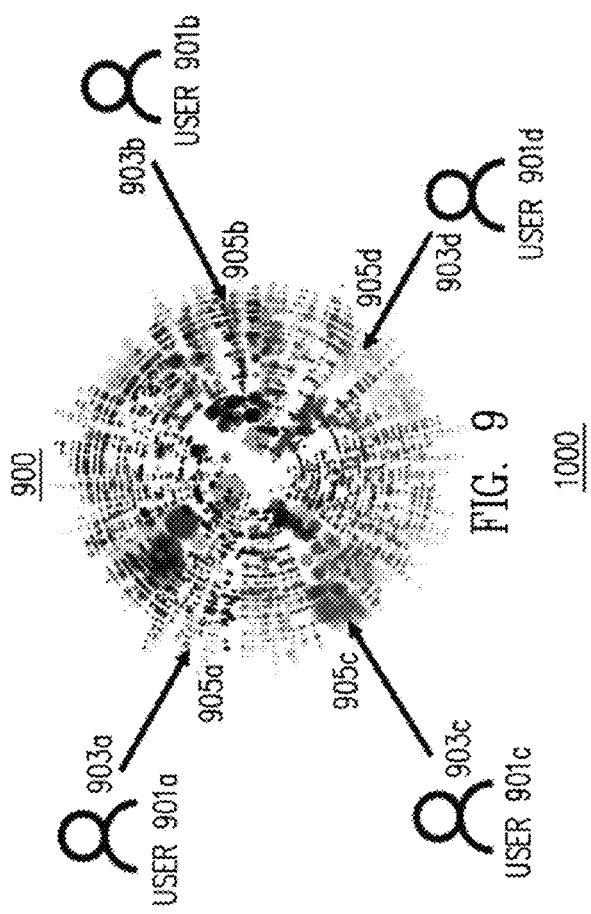
FIG. 9 is an example of a visual data representation created from user and activity data obtained from multiple users, in accordance with one embodiment.

FIG. 9 is an example of a visual data representation 900 generated from user data and user activity data obtained from multiple users, in accordance with one embodiment.

As show in the illustrative example of FIG. 9A, visual data representation 900 is comprised of inputs received from multiple users, such as user 901a, user 901b, user 901c, and user 901d. In the illustrative embodiment of FIG. 9, user 901a contributes raw user data 903a, which is transformed into a unique data representation segment 905a of visual data representation 900. User 901b contributes raw user data 903b, which is transformed into a unique data representation segment 905b of visual data representation 900. User 901c contributes raw user data 903c, which is transformed into a unique data representation segment 905c of visual data representation 900. User 901d contributes raw user data 903d, which is transformed into a unique data representation segment 905d of visual data representation 900.

Figure 10:
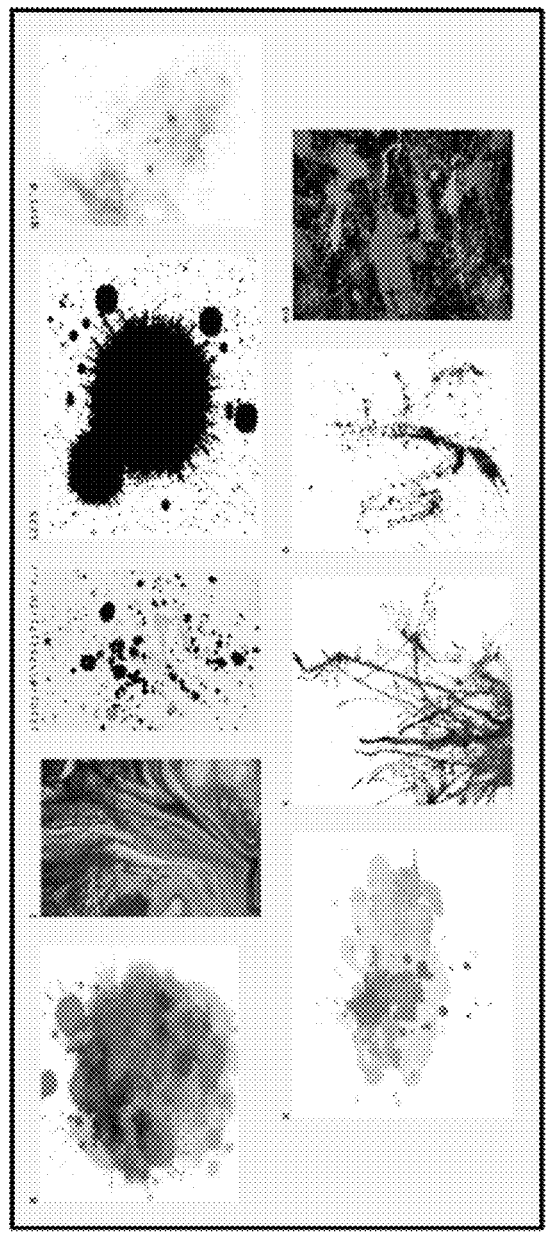
FIG. 10 is an example of various styles of visual data representations created from user data and user activity data obtained from either a single user or multiple users, in accordance with one embodiment.

FIG. 10 is an example of various styles of visual data representations 1000 created from user and activity data obtained from either a single user or multiple users, in accordance with one embodiment. As can be seen from the visual data representations 1000 shown in FIG. 10, there are multiple possibilities for collaboration among multiple users in generating these images. For example, each user's data could be represented by a different color, and the various data representation parameters such as line, curves, and shapes could be defined based on each user's physiological and motion data.

The capability of the method and system disclosed herein to allow for collaborative work on generating a data representation has many potential uses. For example, a group of friends who work out together would be able to create a shared data representation, which may be kept as a memento of the time the friends spent together. Members of an exercise class could work together to create a community mural based on their exercise activity. The collaboration could be done in-person, or remotely, with groups of people over the internet. Furthermore, in the case of real-time data representation generation, the one or more users could watch their work of art being created in front of them, while they are engaging in the activity, thus fostering a sense of community and providing shared goals to work towards.

Other possibilities include creation of data representations to represent sports games. For example, data may be received and/or collected from one or more players on one or more sports teams, and this data may then be transformed into a data representation of a match or a game played between teams. As noted above, and especially in the sports world, the activity of individuals and teams is typically measured by vast quantities of numbers and statistics, which can lead individuals to feel depressed and/or discouraged by creating the impression that their self-worth is being determined by a set of statistics and/or numerical values. By transforming the vast quantities of available data into artwork, individuals may be made to feel that their contributions to a team are more valuable, which can lead to greater feelings of emotional well-being.

Returning now to FIG. 2B, as evidenced by the above discussion, the system and method disclosed herein is capable of taking into account a wide variety of data inputs, such as, but not limited to, those represented as raw user data 260 in FIG. 2B. Further, the data inputs may be collected and/or received from either a single user or from multiple users, and then utilized to transform the raw user data 260 into one or more individual data representations and/or one or more collaborative data representations, which may then be provided to the users either in real-time during the activity, and/or after completion of the activity. The process of transforming the raw user data 260 into one or more data representations will be discussed in additional detail below. As mentioned above, the raw user data 260 may be classified in any number of ways to organize the data for compatibility with a variety of mathematical models, which will be utilized to generate the one or more data representations.

It should be noted again here that the above groupings and classifications of raw user data 260 shown in FIG. 2B are given for illustrative purposes only, and are not meant to limit the scope of the invention as disclosed and as claimed herein. One of skill in the art should readily appreciate that there are many different ways to organize, group, and/or classify raw user data 260, and the organization, grouping, and/or classification may be based on any number of factors, including the type of data representation to be generated, the specific mathematical models to be used, as well as the underlying structure of the application data architecture.

Referring now to FIG. 2A and FIG. 2B together, once raw user data 260 is collected from user 201 and stored in a data structure, such as user database 222, user data aggregation module 250 aggregates raw user data 260 to generate aggregated user and activity data 252. In various embodiments, aggregating raw user data 260 includes formatting raw user data 260 such that it can be provided as inputs to one more mathematical models.

In various embodiments, mathematical model database 238 contains a repository of mathematical models that can be utilized to transform raw user data 260 into one or more data representations. As discussed above, in various embodiments, a mathematical model may include a mathematical based system, such as a mathematical algorithm, function, and/or formula, that takes in one or more data inputs and processes the data inputs in a predefined manner to transform the data inputs into one or more data outputs, wherein the data outputs are transformed representations of the data inputs.

In the illustrative embodiment of FIG. 2A, mathematical model database 238 contains different categories of mathematic models, including visual data representation models 240, audio data representation models 242, textual data representation models 244, and physical data representation models 246. In one embodiment, mathematical model selection module 248 utilizes aggregated user and activity data 252 to select one or more mathematical models, thereby resulting in selected mathematical models 249. As one illustrative example, user 201 may indicate through user input data 218, what type of data representation they would like to have generated, for instance, user 201 might indicate that they would like a visual data representation that represents user 201's physical activity over the course of a year, such as that discussed above with respect to FIG. 5A through FIG. 5D. In one embodiment, the indication is made prior to user 201 initiating an activity and this data is stored in user database 222 as pre-activity user input data 228. Collecting the user preference data prior to initiation of an activity allows for the possibility of the data representation being generated in real time, for example, as user activity physiological data 232 and user activity motion data 234 is being collected from user 201. In one embodiment, the indication is made after user 201 completes an activity and this data is stored in user database 222 as post-activity user input data 230. In one embodiment, collecting the user preference data after completion of an activity may allow for multiple data representations to be generated based on the same user activity physiological data 232 and user activity motion data 234. For example, after completion of an activity, user 201 may select to have the data represented in a fractal visual style, or an inkblot visual style, or may instead choose to have the data represented as a 3D physical model, such as a sculpture or a figurine.

It should be obvious to one of ordinary skill in the art from the above description that a mathematical model utilized to create one type of data representation, such as a visual data representation will be much different than a mathematical model utilized to create another type of data representation, such as a physical data representation. For instance, each type of mathematical model will likely require different inputs in order to generate the data representation. Furthermore, several different mathematical models may be utilized to generate a single data representation, as will be discussed in additional detail below.

In one embodiment, once mathematical model selection module 248 has selected one or more selected mathematical models 249, at least a portion of the aggregated user and activity data 252 is provided as inputs to selected mathematical models 249. In one embodiment, the output of the selected mathematical models is one or more data values, such as, but not limited to, numerical values, which are then passed to user activity data representation parameter mapping module 254. In one embodiment, user activity data representation parameter mapping module 254 takes the output of the selected mathematical models 249 and maps the data values to a variety of user activity data representation parameters 255.

As noted above, user activity data representation parameters 255 may include variables that are utilized to define various data representations. For example, a visual and/or physical data representation may be defined by parameters such as, but not limited to, shape, line, curve, pattern, texture, material, color, tone, contrast, lighting, viewpoint, depth, balance, and/or use of space. An audio data representation may defined by parameters such as, but not limited to, melody, harmony, rhythm, tempo, texture, dynamics, pitch, form, and timbre. A textual data representation may be defined by parameters such as, but not limited to, theme, mood, imagery, character, setting, word choice, repetition, and rhyme.

As one illustrative example, user activity motion data 234 may contain user 201's acceleration and step count during an activity, and user activity physiological data 232 may contain data indicating user 201's heart rate and sweat output during the activity. One or more mathematical models may be selected that will be utilized to transform user 201's data into a visual representation based on activity intensity. One of the selected mathematical models 249 may take some of aggregated user and activity data 252, such as acceleration, step count, heart rate, and sweat output, as inputs, and may process the data according to the model definition. For example, in one embodiment, the first selected mathematical model 249 may take the root means square of each input and average them together to get a value that corresponds to the intensity of the workout. Another of the selected mathematical models 249 may take user 201's data and process the data according to an appropriate formula in order to generate an array or list of (x,y) coordinates to be used for drawing the lines and/or curves that make up the visual data representation. In various embodiments, one or more transformation mathematical models may be utilized, such as, but not limited to, a polar coordinates transformation model, a cylindrical coordinates transformation model, and/or a spherical coordinates transformation model. The outputs of the one or more mathematical models may then be passed to user activity data representation parameter mapping module 254, which may determine, for example, that workout intensity values should be mapped to colors of the visual data representation.

For example, portions of a physical activity, such as a workout, may be more intense than others, and in one embodiment, high intensity activity may be mapped to shades of red, while low intensity activity may be mapped to shades of blue. In other embodiments, high intensity activity may be mapped to other user activity data representation parameters 255, such as, but not limited to, the length or height of a line or a shape, and/or the darkness or lightness of a shape in the visual data representation.

FIG. 11 is a table 1100 showing a simplified example of one way that raw user data can be mapped to colors of a visual and/or physical data representation, in accordance with one embodiment. For example, raw user data indicating exercise intensity, mood, nutrition, sleep quality, and motivation may be provided to one or more mathematical models to generate a numerical value between 0 and 10 for each item of data. The numerical values may then be utilized to determine the shade of a particular color to be used in the data representation. For example, in the illustrative embodiment of FIG. 11, a low value for exercise intensity may be mapped to a lighter shade of red, whereas a high value for exercise intensity may be mapped to a darker shade of red. Mood values may be mapped on a spectrum of white to grey to black. A low value for nutrition may be mapped to a lighter shade of green, whereas a high value for nutrition may be mapped to a darker shade of green. A low value for sleep quality may be mapped to a lighter shade of yellow, whereas a high value for sleep quality may be mapped to a darker shade of yellow. A low value for motivation may be mapped to a lighter shade of blue, whereas a high value for motivation may be mapped to a darker shade of blue. Each piece of raw user data may be defined either by data entered by the user, and/or by data measured from various sensors and/or devices associated with the user, as discussed above. It should be noted again, that the above simplified example is given for illustrative purposes only, and is not intended to limit the scope of the invention as disclosed and/or as claimed herein.

Returning now to FIG. 2A and FIG. 2B together, in the case of an audio data representation, user activity data representation parameter mapping module 254 may map activity intensity to an audio parameter, such as, but not limited to, the loudness or tempo of an audio recording. For instance, high intensity activity may be mapped to a higher audio volume and/or a faster tempo, while low intensity activity may be mapped to a lower audio volume and/or a slower tempo. In the case of a physical data representation, one of the selected mathematical models 249 may process aggregated user and activity data 252 to generate an array or list of (x,y,z) coordinates to be used for constructing a 3D model.

It should be noted that the above examples are given for illustrative purposes only. One of skill in the art will readily recognize that many different mathematical models may be used to transform user 201's data in different ways. Depending on the desired type of data representation and the selected mathematical models 249, almost limitless combinations of parameters can be combined to allow user activity data representation generation module 256 to generate one or more data representations that are completely unique to each user 201, and/or to each activity session. In various embodiments, user activity data representation generation module 256 combines user activity data representation parameters 255 to generate one or more user activity data representation definitions 258, which, in one embodiment, includes data defining one more data representations, such as visual data representation 272, audio data representation 274, textual data representation 276, and/or physical data representation 278, as shown in FIG. 2B.

In various embodiments, user activity data representation generation module 256 provides user activity data representation parameters 258 to one or more generative art application programming interfaces (APIs), which utilize a variety of techniques well-known to those of skill in the art, in order to transform user activity data representation parameters 258 into one or more data representations, such as visual data representation 272, audio data representation 274, textual data representation 276, and/or physical data representation 278, as discussed above.

In embodiment, once user activity data representation generation module 256 has generated user activity data representation definitions 258, one or more of the user activity data representations may be provided to user 201, for instance through user interface 216 of application environment 211. As noted above, in some embodiments, the one or more user activity data representations are provided to user 201 in real-time, during an activity session, while in other embodiments, the one or more user activity data representations are provided to user 201 at some point after completion of an activity session.

In the case of a visual data representation, which may include still images, animations, and/or videos, the visual data representation may be exported to any number of image and/or video formats, such as, but not limited to, JPG, PNG, TIFF, GIF, PDF, MP4, MOV, WMV, and/or AVI formats, which may then be provided to user 201. In the case of an audio data representation, which may include songs, musical scores, spoken word recordings, sound effects, and/or ringtones, the audio data representation may be exported to any number of audio formats, such as, but not limited to, MP3, WAV, and OGG formats, which may then be provided to user 201. In the case of a textual data representation, which may include poetry and/or prose, the textual data representation may be exported to any number of textual formats, such as, but not limited to DOC, DOCX, TXT, XLS and/or XLSX formats, which may then be provided to user 201. In the case of a physical data representation, which may include 3D models, sculptures and/or figurines, the physical data representation may exported to any number of formats. For example, the physical data representation may be exported to a digital file format used for 3D rendering and/or printing, such as, but not limited to, STL, OBJ and VRML, and the STL, OBJ and/or VRML file representing the physical data representation may then be provided to user 201. In other embodiments, an STL, OBJ, and/or VRML file may be provided to a 3D printer to create an actual 3D physical model, and the 3D physical model may then be provided to user 201, for instance, delivered to user 201 via a mail and/or parcel delivery service.

In various embodiments, the data representations may be provided to one or more users 201 through any number of means, such as, but not limited to, through email or text message, through a mobile or web application, through a social media platform, through a physical mail and/or parcel delivery service and/or any other type of communications mechanism discussed herein, known at the time of filing, developed/made available after the time of filing, or any combination thereof.

It should be noted again here that the above simplified examples are given for illustrative purposes only and are not intended to limit the invention as disclosed and claimed herein. It should be readily apparent to those of ordinary skill in the art that there are millions of potential combinations of user data, user activity data, mathematical models, and/or data representation parameters that may be utilized to transform user data into artistic and/or other types of data representations, and so the generation of unique data representations that takes into account all of the above noted factors is not a task that can be accomplished in the human mind, even with pen and paper, and even given unlimited time.

Process

Figure 12:
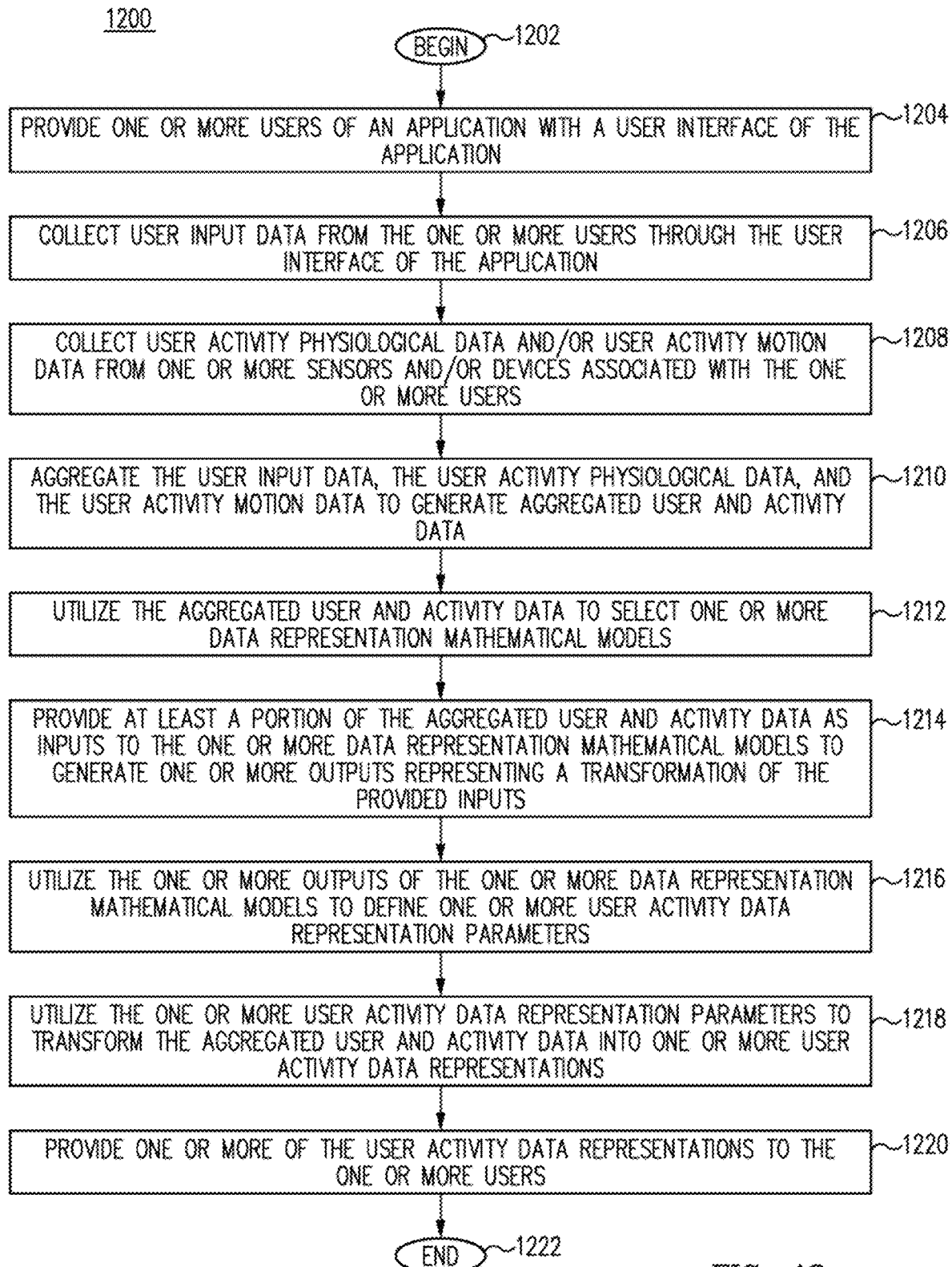
FIG. 12 is a flow chart of a process for transforming user data and user activity data into various data representations, in accordance with one embodiment.

FIG. 12 is a flow chart of a process 1200 for transforming user data and user activity data into various data representations, in accordance with one embodiment.

Process 1200 begins at BEGIN 1202 and process flow proceeds to 1204. In one embodiment, at 1204, one or more users of an application are provided with a user interface of the application.

In one embodiment, the application is designed to facilitate collection of data associated with the user, in order to transform the user data into unique and/or artistic visual, audio, textual and/or physical data representations, which can be generated and provided to the user in a digital and/or physical format. In one embodiment, a user interface of the application is provided to the user via one or more user computing systems. In various embodiments, user computing systems may include, but are not limited to, a desktop computing system, a mobile computing system, a virtual reality computing system, a gaming computing system, a computing system that utilizes one or more Internet of Things (IoT) devices, and/or any other type of computing system discussed herein, known at the time of filing, developed/made available after the time of filing, or any combination thereof.

In one embodiment, once one or more users of an application are provided with a user interface of the application at 1204, process flow proceeds to 1206. In one embodiment, at 1206, user input data is collected from the one or more users through the user interface of the application.

In one illustrative embodiment, the user may sign into the application via the user interface, and the user may first be presented with a welcome screen. Upon selection of an option to begin, the user may then be prompted to answer several questions prior to beginning the chosen physical activity. If it is the first time the user is utilizing the application, user input data may be requested, which in some embodiments includes user profile data, such as name, age, gender, weight, and activity level. In some embodiments, prior to beginning a physical activity, additional user input data may be collected. For example, the user may input data related to date and time associated with the activity, data related to the lifestyle of the user, data related to the event and/or physical activity that is to be monitored, and/or various preferences, such as preferences for the type of data transformation to perform. In some embodiments, user input data is collected prior to the user beginning a physical activity, while in some embodiments, user input data is collected after completion of a physical activity. In some embodiments, only pre-activity user input data is collected. In some embodiments, only post-activity user input data is collected. In some embodiments, both pre-activity user input data and post-activity user input data are collected. In some embodiments, neither pre-activity user input data nor post-activity user input data is collected, and a variety of default settings may instead be utilized to transform data received from user sensors and devices into one or more data representations.

In one embodiment, once user input data is collected from the one or more users through the user interface of the application at 1206, process flow proceeds to 1208. In one embodiment, at 1208, user activity physiological data and/or user activity motion data is collected from one or more sensors and/or devices associated with the one or more users.

In one embodiment, at 1208, collection of physiological and motion data associated with the user during performance of a physical activity is initiated, and the user may be presented with one or more user interface screens. In one embodiment a user interface screen presents the user with an animated GIF or video showing the user that they are creating a data representation, such as an artistic representation, while the user is engaging in the activity.

In various embodiments, user activity physiological data and/or user activity motion data is collected from the user via one or more user sensors and/or devices and the data is stored locally within the user sensors and/or devices, and/or the data is transmitted to a server over one or more communications channels. In one embodiment, one or more user sensors and devices are attached to or are in close proximity to the user. In one embodiment, user sensors and devices may include sensors and devices such as, but not limited to, a smart phone, a smart watch, a tablet, a laptop computing system, a desktop computing system, an Internet of Things (IoT) device, and/or computing systems and sensors that may be incorporated into exercise equipment. In various embodiments, user sensors and devices may further include sensors and devices such as accelerometers, gyroscopes, global positioning system (GPS) devices, heart rate monitors, blood pressure monitors, blood oxygen level monitors, epidermal sensors, electromyograph devices, blood testing devices, and/or any other devices capable of collecting user physiological and/or motion data, as discussed herein, known at the time of filing, and/or developed/made available after the time of filing. In various embodiments, user activity physiological data may include data such as, but not limited to, user heart rate, respiratory rate, blood pressure, blood oxygen level, skin and/or body temperature, sweat output, muscle activity, sleep quality, and/or calorie burn. In various embodiments user activity motion data may include data such as, but not limited to, user speed, acceleration, velocity, revolutions per minute, changes in altitude of the user's body and/or the user's individual body parts, changes in location and/or direction of the user's body and/or the user's individual body parts and/or changes in the user's geographical location.

In one embodiment, after the user has indicated completion of an activity, such as through a user interface screen of the application, the collected user activity physiological data and user activity motion data may be stored in a data structure for further processing. In one embodiment, user activity physiological data and user activity motion data is collected by user sensors and/or devices during the activity, but is not transmitted for further processing until after the activity is completed. In this situation, the resulting data representations may be generated and provided to the user after completion of the activity. In other embodiments, user activity physiological data and user activity motion data are transmitted for processing in real-time. In the case of real-time data transmission, the resulting data representations may then be provided to the user in real-time, for instance, through a user interface screen of the application, such that the user can watch the data representation change and/or grow as it is being generated.

In one embodiment, once user activity physiological data and/or user activity motion data is collected from one or more sensors and/or devices associated with the one or more users at 1208, process flow proceeds to 1210. In one embodiment, at 1210, the user input data, the user activity physiological data, and the user activity motion data are aggregated to generate aggregated user and activity data.

As discussed above various types of data may be received and/or collected from the user and aggregated to generate aggregated user and activity data. For example, in one embodiment, aggregated user and user activity data may include user profile data, current user activity data, and historical user activity and representation data. Current user activity data may further include pre-activity user input data, post-activity user input data, user activity physiological data, and user activity motion data. In various embodiments, aggregated user and user activity data may be referred to as raw user data. In various embodiments, some of the raw user data can be classified as objective data, which can typically best be measured by sensors and/or devices associated with the user, while some of the raw user data can be classified as subjective data, which can typically best be measured by collecting user input data directly from the user. In some embodiments, the raw user data may have both subjective and objective components. In various embodiments, the raw user data may be collected from manually entered user input data and/or the raw user data may be obtained automatically via any number of sensors and/or devices.

In various embodiments, aggregated user and activity data may include user profile data such as, but not limited to, the user's name, age, gender, weight, fitness level, and fitness goals. In various embodiments, pre-activity user input data may be collected prior to the start of an activity session and/or post-activity user input data may be collected after the completion of an activity session. In various embodiments, examples of pre-activity user input data, and post-activity user input data include user event data, user time data, user lifestyle data, and user transformation type data. In various embodiments, user event data may include data related to activity events/sessions associated with the user. For example, user event data may include data such as, but not limited to, the type of activity the user engaged in, the duration of the activity the user engaged in, the intensity of the activity the user engaged in, the number of participants that engaged in the activity, as well as a variety of performance metrics related to the activity.

In various embodiments, user time data may include data such as the time and date of the physical activity, the season during which the physical activity event took place, and/or the user may specify periods of time, or divisions of time, which may be utilized to determine what data is to be used for generating a data representation. In various embodiments, user lifestyle data may include user input data received and/or collected from the user relating to user mood, user mindset, user exercise habits, user nutrition/eating habits, user sleep habits, and/or user social habits. In various embodiments, user transformation type data may include user preference data related to the type of data representation that the user wishes to transform the user data and user activity data into. In various embodiments, aggregated user and activity data further includes user activity physiological data such as, but not limited to, the user heart rate, respiratory rate, blood pressure, blood oxygen level, skin and/or body temperature, sweat output, muscle activity, sleep quality, and calorie burn. In various embodiments aggregated user and activity data further includes user activity motion data such as, but not limited to, user speed, acceleration, velocity, revolutions per minute, changes in altitude of the user's body and/or individual body parts, changes in location and/or direction of the user's body and/or individual body parts, and/or changes in the user's geographical location. In one embodiment, aggregated user and activity data may also include historical user activity and representation data, which may include any collected data associated with the user past activities, as well as any data related to past data representations generated for the user.

In some embodiments, aggregated user and activity data is received and/or collected only for a single user, and the resulting data representation is generated based solely on the one user's data inputs. In other embodiments, data is received and/or collected from multiple users, and the resulting data representation may be generated based on data inputs from each user and/or based on data inputs from a subset of the multiple users. In various embodiments, aggregating user data and user activity data includes formatting the user data and user activity such that it can be provided as inputs to one or more mathematical models.

In one embodiment, once the user input data, the user activity physiological data, and the user activity motion data are aggregated at 1210, process flow proceeds to 1212. In one embodiment, at 1212, the aggregated user and activity data is utilized to select one or more data representation mathematical models.

In various embodiments, a variety of mathematical models can be utilized to transform aggregated user and activity data into one or more data representations. As noted above, a mathematical model may include a mathematical based system, such as a mathematical algorithm, function, and/or formula, that takes in one or more data inputs and processes the data inputs in a predefined manner to transform the data inputs into one or more data outputs, wherein the data outputs are transformed representations of the data inputs, such as, but not limited to, one or more numerical values.

Some mathematical models can be utilized to generate visual data representations, audio data representations, textual data representations, and physical data representations. In one embodiment, one or more mathematical models are selected based on aggregated user and activity data. It should be obvious to one of ordinary skill in the art from the above discussion that a mathematical model utilized to create one type of data representation, such as a visual data representation, will be much different than a mathematical model utilized to create another type of data representation, such as a physical data representation. For instance, each type of mathematical model will likely require different inputs in order to generate the data representation. Furthermore, several different mathematical models may be utilized to generate a single data representation.

In one embodiment, once the aggregated user and activity data is utilized to select one or more data representation mathematical models at 1212, process flow proceeds to 1214. In one embodiment, at 1214, at least a portion of the aggregated user and activity data is provided as inputs to the one or more data representation mathematical models to generate one or more outputs based on a transformation of the provided inputs.

In one embodiment, once one or more data representation mathematical models are selected, at least a portion of the aggregated user and activity data is provided as inputs to the selected mathematical models. In one embodiment, the output of the selected mathematical models is one or more numerical values, which are numerical representations of the input data. For example, in one embodiment, one selected mathematical model may process the input data in a number of ways, such as, but not limited to, taking the root means square of each input, such as acceleration, step count, heart rate, and sweat output, and averaging them together to get a numerical value that corresponds to the intensity of the workout. Another of the selected mathematical models may take the user's data as inputs and process the user's data according to an appropriate formula in order to generate an array or list of (x,y) coordinates to be used for drawing the lines and/or curves that make up the visual data representation.

In one embodiment, once one or more outputs are generated based on a transformation of the inputs provided to the one or mathematical models at 1214, process flow proceeds to 1216. In one embodiment, at 1216, the outputs of the one or more data representation mathematical models are utilized to define one or more user activity data representation parameters.

In various embodiments, the user activity data representation parameters are defined by mapping the outputs of the one or more data representation mathematical models to a variety of data representation parameters. As noted above, user activity data representation parameters may include variables that are utilized to define various data representations. For example, a visual and/or physical data representation may be defined by parameters such as, but not limited to, shape, line, curve, pattern, texture, material, color, tone, contrast, lighting, viewpoint, depth, balance, and/or use of space. An audio data representation may defined by parameters such as, but not limited to, melody, harmony, rhythm, tempo, texture, dynamics, pitch, form, and timbre. A textual data representation may be defined by parameters such as, but not limited to, theme, mood, imagery, character, setting, word choice, repetition, and rhyme.

As one simplified example, in the case of a visual data representation, a selected mathematical model may determine values representing one or more user data variables such as exercise intensity, mood, nutrition, sleep quality, and motivation, and each of these variables may be mapped to a visual data representation parameter, such as, but not limited to, color, shape, line, curve, or pattern. In the case of an audio data representation, these same data variables may be mapped to an audio data representation parameter, such as, but not limited to, the loudness or tempo of an audio recording.

In one embodiment, once the outputs of the one or more data representation mathematical models are utilized to define one or more user activity data representation parameters at 1216, process flow proceeds to 1218. In one embodiment, at 1218, the one or more user activity data representation parameters are utilized to transform the aggregated user and activity data into one or more user activity data representations.

In various embodiments, the one or more user activity data representation parameters are provided to one or more generative art application programming interfaces (APIs), which utilize a variety of techniques in order to transform the user activity data representation parameters into one or more data representations, such as visual, audio, textual, and/or physical data representations discussed above.

In one embodiment, once the one or more user activity data representation parameters are utilized to transform the aggregated user and activity data into one or more user activity data representations at 1218, process flow proceeds to 1220. In one embodiment, at 1220, one or more of the user activity data representations are provided to the one or more users.

In embodiment, once one or more user activity data representations have been generated, one or more of the user activity data representations may be provided to the user, for instance through the user interface of the application. In the case of a visual data representation, which may include still images, animations, and/or videos, the visual data representation may be exported to any number of image and/or video formats, which may then be provided to the user. In the case of an audio data representation, which may include songs, musical scores, spoken word recordings, sound effects, and/or ringtones, the audio data representation may be exported to any number of audio formats, which may then be provided to the user. In the case of a textual data representation, which may include poetry and/or prose, the textual data representation may be exported to any number of textual formats, which may then be provided to the user. In the case of a physical data representation, which may include 3D models, sculptures and/or figurines, the physical data representation may exported to any number of formats. For example, the physical data representation may be exported to a digital file format used for 3D rendering and/or printing, and a file representing the physical data representation may then be provided to the user. In other embodiments, a file representing the physical data representation may be provided to a 3D printer to create an actual 3D physical model, and the 3D physical model may then be provided and/or delivered to the user.

In various embodiments, the data representations may be provided to the one or more users through any number of means, such as, but not limited to, through email or text message, through a mobile or web application, through a social media platform, and/or through a physical mail and/or parcel delivery service and/or any other type of communications mechanism discussed herein, known at the time of filing, developed/made available after the time of filing, or any combination thereof.

In one embodiment, once one or more of the user activity data representations are provided to the one or more users at 1220, process flow proceeds to END 1222 and the process 1200 for transforming user data and user activity data into various data representations is exited to await new data and/or instructions.

In the disclosed embodiments, a computing system implemented method comprises providing one or more users, or an individual user, of an application with a user interface of the application, collecting user input data from the one or more users, or the individual user, through the user interface of the application, collecting user activity physiological data associated with the one or more users or the individual user, and collecting user activity motion data associated with the one or more users or the individual user. In one embodiment, the method further includes aggregating the user input data, the user activity physiological data, and the user activity motion data to generate aggregated user and activity data, and utilizing the aggregated user and activity data to select one or more data representation mathematical models. In one embodiment, the method further includes providing at least a portion of the aggregated user and activity data as inputs to the one or more data representation mathematical models to generate one or more outputs based on a transformation of the provided inputs, utilizing the one or more outputs of the one or more data representation mathematical models to define one or more user activity data representation parameters, utilizing the one or more user activity data representation parameters to transform the aggregated user and activity data into one or more user activity data representations, and providing one or more of the user activity data representations to the one or more users or the individual user.

In one embodiment, the one or more user activity data representations include one or more of a visual data representation, an audio data representation, a textual data representation; and a physical data representation.

In one embodiment, the user activity physiological data includes one or more of heart rate, respiratory rate, blood pressure, blood oxygen level, skin temperature, body temperature, sweat output, muscle activity, calorie burn, sleep quality, and nutrition. In one embodiment, the user activity physiological data is collected from one or more of data entered by a user, heart rate monitoring devices, blood pressure monitoring devices, blood oxygen level monitoring devices, skin temperature monitoring devices, body temperature monitoring devices, epidermal sensor devices, electromyograph devices, sleep-tracking devices, and blood testing devices.

In one embodiment, the user activity motion data includes one or more of speed, acceleration, velocity, revolutions per minute, changes in altitude of a user's body, changes in altitude of a user's individual body parts, changes in location of a user's body, changes in location of a user's individual body parts, and changes in a user's geographical location. In one embodiment, the user activity motion data is collected from one or more of data entered by a user, accelerometer devices, gyroscope devices, and global positioning system (GPS) devices.

In one embodiment, the one or more mathematical models include mathematical models selected from the group of mathematical models consisting of a root means square mathematical model, a polar coordinates transformation mathematical model, a cylindrical coordinates transformation mathematical model, and a spherical coordinates transformation mathematical model. In one embodiment, the user activity data representation parameters include one or more of shape, line, curve, pattern, texture, material, color, tone, contrast, lighting, viewpoint, depth, balance, use of space, melody, harmony, rhythm, tempo, texture, dynamics, pitch, form, timbre, theme, mood, imagery, character, setting, word choice, repetition, and rhyme.

In one embodiment, the one or more user activity data representations are generated based on data inputs from a single user. In one embodiment, the one or more user activity data representations are generated based on data inputs from multiple users. In one embodiment, the one or more user activity data representations are provided in real-time to the one or more users.

In one embodiment, a system comprises an application having a user interface for interacting with the application, one or more databases, the one or more databases including user profile data, user input data, user activity physiological data, user activity motion data, and mathematical model data, one or more devices associated with the user of the application, one or more sensors associated with the user of the application, one or more processors, and one or more physical memories, the one or more physical memories having stored therein data representing instructions, which when processed by the one or more processors perform the above described computer implemented method/process.

As discussed above, the above described method and system uses various technological methods to collect user data and user activity data from one or more users of an application and the user data and user activity data is utilized to generate a variety of visual, audio, textual, and/or physical data representations, which may be provided to the one or more users either dynamically in real-time during an activity, such as a physical exercise activity, or may be provided to the one or more users after the completion of one or more activities. The goal is to help motivate individuals to maintain healthy exercise, nutritional, and social routines by dynamically generating individualized artistic data representations that are unique to one or more activity sessions of a particular user and/or particular group of users. As a result of these and other disclosed features, discussed in detail above, the disclosed embodiments provide an effective and efficient technical solution to the technical problem of transforming health and exercise-related data received and/or collected from individuals into one or more individualized and unique data representations in order to inspire and motivate individuals to maintain healthy lifestyles while engaging in activities that foster the growth and development of social connections through participation in a shared artistic goal.

Consequently, the embodiments disclosed herein are not an abstract idea, and are well-suited to a wide variety of practical applications. Further, many of the embodiments disclosed herein require processing and analysis of millions of potential combinations of user data, user activity data, mathematical models, and/or data representation parameters, in order to generate digital and/or physical data representations, and thus, the technical solution disclosed herein cannot be implemented solely by mental steps or pen and paper, is not an abstract idea, and is, in fact, directed to providing technical solutions to long-standing technical problems associated with dynamically transforming received and/or collected user data into unique artistic and/or other types of data representations.

Additionally, the disclosed method and system for dynamically transforming raw data obtained from one or more users into one or more individualized and unique data representations requires a specific process comprising the aggregation and detailed analysis of large quantities of user data, user activity data, mathematical models, and/or data representation parameters, and as such, does not encompass, embody, or preclude other forms of innovation in the area of dynamically generating data representations. Further, the disclosed embodiments of systems and methods for dynamically transforming raw data obtained from one or more users into one or more individualized and unique data representations are not abstract ideas for at least several reasons.

First, dynamically transforming raw data obtained from one or more users into one or more individualized and unique data representations is not an abstract idea because it is not merely an idea in and of itself. For example, the process cannot be performed mentally or using pen and paper, as it is not possible for the human mind to identify, process, and analyze the millions of potential combinations of user data, user activity data, mathematical models, and/or data representation parameters to generate unique data representations based on that data, even with pen and paper to assist the human mind and even with unlimited time.

Second, dynamically transforming raw data obtained from one or more users into one or more individualized and unique data representations is not a fundamental economic practice (e.g., is not merely creating a contractual relationship, hedging, mitigating a settlement risk, etc.).

Third, dynamically transforming raw data obtained from one or more users into one or more individualized and unique data representations is not merely a method of organizing human activity (e.g., managing a game of bingo). Rather, in the disclosed embodiments, the method and system for dynamically transforming raw data obtained from one or more users into one or more individualized and unique data representations provides a tool that significantly improves the fields of physical and mental health care. Through the disclosed embodiments, individuals are provided with a tool to help them generate motivational artwork through exercise, which encourages individuals to maintain healthy lifestyles while engaging in activities that foster the growth and development of social connections.

As such, the method and system disclosed herein is not an abstract idea, and also serves to integrate the ideas disclosed herein into practical applications of those ideas.

Fourth, although mathematics may be used to implement the embodiments disclosed herein, the systems and methods disclosed and claimed herein are not abstract ideas because the disclosed systems and methods are not simply a mathematical relationship/formula.

It should be noted that the language used in the specification has been principally selected for readability, clarity, and instructional purposes, and may not have been selected to delineate or circumscribe the inventive subject matter. Accordingly, the disclosure of the present invention is intended to be illustrative, but not limiting, of the scope of the invention, which is set forth in the claims below.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, or protocols. Further, the system or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of ordinary skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

As discussed in more detail above, using the above embodiments, with little or no modification and/or input, there is considerable flexibility, adaptability, and opportunity for customization to meet the specific needs of various parties under numerous circumstances.

Some portions of the above description present the features of the present invention in terms of algorithms and symbolic representations of operations, or algorithm-like representations, of operations on information/data. These algorithmic or algorithm-like descriptions and representations are the means used by those of skill in the art to most effectively and efficiently convey the substance of their work to others of skill in the art. These operations, while described functionally or logically, are understood to be implemented by computer programs or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as, but not limited to, "activating", "accessing", "adding", "aggregating", "alerting", "applying", "analyzing", "associating", "calculating", "capturing", "categorizing", "classifying", "comparing", "creating", "defining", "detecting", "determining", "distributing", "eliminating", "encrypting", "extracting", "filtering", "forwarding", "generating", "identifying", "implementing", "informing", "monitoring", "obtaining", "posting", "processing", "providing", "receiving", "requesting", "saving", "sending", "storing", "substituting", "transferring", "transforming", "transmitting", "using", etc., refer to the action and process of a computing system or similar electronic device that manipulates and operates on data represented as physical (electronic) quantities within the computing system memories, resisters, caches or other information storage, transmission or display devices.

The present invention also relates to an apparatus or system for performing the operations described herein. This apparatus or system may be specifically constructed for the required purposes, or the apparatus or system can comprise a system selectively activated or configured/reconfigured by a computer program stored on a non-transitory computer readable medium for carrying out instructions using a processor to execute a process, as discussed or illustrated herein that can be accessed by a computing system or other device.

Those of ordinary skill in the art will readily recognize that the algorithms and operations presented herein are not inherently related to any particular computing system, computer architecture, computer or industry standard, or any other specific apparatus. Various systems may also be used with programs in accordance with the teaching herein, or it may prove more convenient/efficient to construct more specialized apparatuses to perform the required operations described herein. The required structure for a variety of these systems will be apparent to those of ordinary skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the invention as contemplated by the inventors at the time of filing.

The present invention is well suited to a wide variety of computer network systems operating over numerous topologies. Within this field, the configuration and management of large networks comprise storage devices and computers that are communicatively coupled to similar or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the figures, or as discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented method comprising:
providing one or more users of an application with a user interface of the application;
collecting user input data from the one or more users through the user interface of the application;
based on the user input data, selecting one or more user activity data representation types to be generated for each of the one or more users;
based on the selected one or more user activity data representation types, selecting one or more data representation mathematical models;
utilizing one or more sensor devices to collect user activity physiological data associated with the one or more users during performance of one or more physical activities;
utilizing one or more sensor devices to collect user activity motion data associated with the one or more users during performance of one or more physical activities;
aggregating the user input data, the user activity physiological data, and the user activity motion data to generate aggregated user and activity data;

providing at least a portion of the aggregated user and activity data as inputs to the one or more data representation mathematical models to generate one or more outputs based on a transformation of the provided inputs;

mapping one or more outputs of the one or more data representation mathematical models to one or more user activity data representation parameters, wherein the values of the one or more user activity data representation parameters determine compositional elements for individualization of one or more user activity data representations;

providing one or more of the user activity data representation parameters to one or more generative art interfaces;

generating, by one or more of the generative art interfaces, one or more individualized user activity data representations based on the values of the one or more user activity data representation parameters; and providing one or more of the individualized user activity data representations to the one or more users.

2. The method of claim 1 wherein the one or more user activity data representations include one or more of:
   a visual data representation;
   an audio data representation;
   a textual data representation; and
   a physical data representation.

3. The method of claim 1 wherein the user activity physiological data includes one or more of:
   heart rate;
   respiratory rate;
   blood pressure;
   blood oxygen level;
   skin temperature;
   body temperature;
   sweat output;
   muscle activity;
   calorie burn;
   sleep quality; and
   nutrition.

4. The method of claim 3 wherein the user activity physiological data is collected from one or more of:
   data entered by a user;
   heart rate monitoring devices;
   blood pressure monitoring devices;
   blood oxygen level monitoring devices;
   skin temperature monitoring devices;
   body temperature monitoring devices;
   epidermal sensor devices;
   electromyograph devices;
   sleep-tracking devices; and
   blood testing devices.

5. The method of claim 1 wherein the user activity motion data includes one or more of:
   speed;
   acceleration;
   velocity;
   revolutions per minute;
   changes in altitude of a user's body;
   changes in altitude of a user's individual body parts;
   changes in location of a user's body;
   changes in location of a user's individual body parts; and
   changes in a user's geographical location.

6. The method of claim 5 wherein the user activity motion data is collected from one or more of:
   data entered by a user;
   accelerometer devices;
   gyroscope devices; and
   global positioning system (GPS) devices.

7. The method of claim 1 wherein the one or more mathematical models include mathematical models selected from the group of mathematical models consisting of:
   a root means square mathematical model;
   a polar coordinates transformation mathematical model;
   a cylindrical coordinates transformation mathematical model; and
   a spherical coordinates transformation mathematical model.

8. The method of claim 1, wherein the user activity data representation parameters include one or more of:
   shape, line, curve, pattern, texture, material, color, tone, contrast, lighting, viewpoint, depth, balance, use of space, melody, harmony, rhythm, tempo, texture, dynamics, pitch, form, timbre, theme, mood, imagery, character, setting, word choice, repetition, and rhyme.

9. The method of claim 1, wherein the one or more user activity data representations are generated based on data inputs from a single user.

10. The method of claim 1, wherein the one or more user activity data representations are generated based on data inputs from multiple users.

11. The method of claim 1, wherein the one or more user activity data representations are provided in real-time to the one or more users.

12. A system comprising:
   an application having a user interface for interacting with the application;
   one or more databases, the one or more databases including user profile data, user input data, user activity physiological data, user activity motion data, and mathematical model data;
   one or more sensor devices associated with one or more users of the application;
   one or more generative art interfaces;
   one or more processors; and
   one or more physical memories, the one or more physical memories having stored therein data representing instructions which when processed by the one or more processors perform a process, the process comprising:
   providing one or more users of the application with the user interface of the application;
   collecting user input data from the one or more users through the user interface of the application;
   based on the user input data, selecting one or more user activity data representation types to be generated for each of the one or more users;
   based on the selected one or more user activity data representation types, selecting one or more data representation mathematical models;
   utilizing the one or more sensor devices to collect user activity physiological data associated with the one or more users during performance of one or more physical activities;
   utilizing the one or more sensor devices to collect user activity motion data associated with the one or more users during performance of one or more physical activities;
   aggregating the user input data, the user activity physiological data, and the user activity motion data to generate aggregated user and activity data;

providing at least a portion of the aggregated user and activity data as inputs to the one or more data representation mathematical models to generate one or more outputs based on a transformation of the provided inputs;

mapping one or more outputs of the one or more data representation mathematical models to one or more user activity data representation parameters, wherein the values of the one or more user activity data representation parameters determine compositional elements for individualization of one or more user activity data representations;

providing one or more of the user activity data representation parameters to one or more generative art interfaces;

generating, by one or more of the generative art interfaces, one or more individualized user activity data representations based on the values of the one or more user activity data representation parameters; and providing one or more of the individualized user activity data representations to the one or more users.

13. The system of claim 12 wherein the one or more user activity data representations include one or more of:
a visual data representation;
an audio data representation;
a textual data representation; and
a physical data representation.

14. The system of claim 12 wherein the user activity physiological data includes one or more of:
heart rate;
respiratory rate;
blood pressure;
blood oxygen level;
skin temperature;
body temperature;
sweat output;
muscle activity;
calorie burn;
sleep quality; and
nutrition.

15. The system of claim 14 wherein the user activity physiological data is collected from one or more of:
data entered by a user;
heart rate monitoring devices;
blood pressure monitoring devices;
blood oxygen level monitoring devices;
skin temperature monitoring devices;
body temperature monitoring devices;
epidermal sensor devices;
electromyograph devices;
sleep-tracking devices; and
blood testing devices.

16. The system of claim 12 wherein the user activity motion data includes one or more of:
speed;
acceleration;
velocity;
revolutions per minute;
changes in altitude of a user's body;
changes in altitude of a user's individual body parts;
changes in location of a user's body;
changes in location of a user's individual body parts; and
changes in a user's geographical location.

17. The system of claim 16 wherein the user activity motion data is collected from one or more of:
data entered by a user;
accelerometer devices;
gyroscope devices; and
global positioning system (GPS) devices.

18. The system of claim 12 wherein the one or more mathematical models include mathematical models selected from the group of mathematical models consisting of:
a root means square mathematical model;
a polar coordinates transformation mathematical model;
a cylindrical coordinates transformation mathematical model; and
a spherical coordinates transformation mathematical model.

19. The system of claim 12, wherein the user activity data representation parameters include one or more of:
shape, line, curve, pattern, texture, material, color, tone, contrast, lighting, viewpoint, depth, balance, use of space, melody, harmony, rhythm, tempo, texture, dynamics, pitch, form, timbre, theme, mood, imagery, character, setting, word choice, repetition, and rhyme.

20. The system of claim 12, wherein the one or more user activity data representations are generated based on data inputs from a single user.

21. The system of claim 12, wherein the one or more user activity data representations are generated based on data inputs from multiple users.

22. The system of claim 12, wherein the one or more user activity data representations are provided in real-time to the one or more users.

23. A computing system implemented method comprising:
providing one or more users of an application with a user interface of the application;
collecting user input data from one or more of the users through the user interface of the application;
based on the user input data, selecting a user activity data representation type;
based on the selected user activity data representation type, selecting one or more data representation mathematical models;
utilizing one or more sensor devices to collect user activity physiological data associated with multiple users during performance of a shared group physical activity;
utilizing one or more sensor devices to collect user activity motion data associated with the multiple users during performance of a shared group physical activity;
aggregating the user input data, the user activity physiological data, and the user activity motion data to generate aggregated user and activity data;
providing at least a portion of the aggregated user and activity data as inputs to the one or more data representation mathematical models to generate one or more outputs based on a transformation of the provided inputs;
mapping one or more outputs of the one or more data representation mathematical models to one or more user activity data representation parameters, wherein the values of the one or more user activity data representation parameters determine compositional elements for generation of a collaborative user activity data representation;
providing one or more of the user activity data representation parameters to one or more generative art interfaces;

generating, by one or more of the generative art interfaces, a collaborative user activity data representation based on the values of the one or more user activity data representation parameters, wherein the activity data associated with each individual one of the multiple users during performance of the shared group physical activity contributes to a unique segment of the collaborative user activity data representation; and providing the collaborative user activity data representation to one or more of the multiple users.

* * * * *